US009233117B2

(12) United States Patent
Jacovella et al.

(10) Patent No.: US 9,233,117 B2
(45) Date of Patent: *Jan. 12, 2016

(54) TREATMENT OF INFLAMMATORY LESIONS OF ROSACEA WITH IVERMECTIN

(71) Applicant: Galderma S.A., Cham (CH)

(72) Inventors: Jean Jacovella, Antibes (FR); Jean-Paul Chappuis, Valbonne (FR); Nathalie Sordello Wagner, Pegomas (FR); Michael Graeber, Lawrenceville, NJ (US); Alexandre Kaoukhov, Newport Beach, CA (US); Laurence Salin, La Roquette sur Siagne (FR); Michel Poncet, Mougins (FR); Philippe Briantais, Antibes (FR); Khaled Benkali, Antibes (FR)

(73) Assignee: Galderma S. A., Cham (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/209,927

(22) Filed: Mar. 13, 2014

(65) Prior Publication Data

US 2015/0011489 A1 Jan. 8, 2015

Related U.S. Application Data

(60) Provisional application No. 61/927,717, filed on Jan. 15, 2014, provisional application No. 61/919,208, filed on Dec. 20, 2013, provisional application No. 61/843,540, filed on Jul. 8, 2013.

(51) Int. Cl.
| | |
|---|---|
| *A61K 31/70* | (2006.01) |
| *A61K 31/7048* | (2006.01) |
| *A61K 31/4174* | (2006.01) |
| *A61K 9/00* | (2006.01) |
| *A61K 31/4164* | (2006.01) |
| *A61K 47/10* | (2006.01) |
| *A61K 47/14* | (2006.01) |
| *A61K 9/06* | (2006.01) |

(52) U.S. Cl.
CPC ........... *A61K 31/7048* (2013.01); *A61K 9/0014* (2013.01); *A61K 9/06* (2013.01); *A61K 31/4164* (2013.01); *A61K 31/4174* (2013.01); *A61K 47/10* (2013.01); *A61K 47/14* (2013.01)

(58) Field of Classification Search
CPC ................................................. A61K 31/7048
See application file for complete search history.

(56) References Cited

U.S. PATENT DOCUMENTS

| | | | |
|---|---|---|---|
| 5,332,577 A | 7/1994 | Gertner et al. | |
| 5,952,372 A | 9/1999 | McDaniel | |
| 6,133,310 A | 10/2000 | Parks | |
| 6,319,945 B1 | 11/2001 | Parks | |
| 6,399,651 B1 | 6/2002 | Parks | |
| 6,399,652 B1 | 6/2002 | Parks | |
| 6,433,006 B2 | 8/2002 | Parks | |
| 6,458,342 B1 | 10/2002 | Heidenfelder et al. | |
| 7,550,440 B2 | 6/2009 | Manetta et al. | |
| 8,080,530 B2 | 12/2011 | Manetta et al. | |
| 8,093,219 B2 | 1/2012 | Manetta et al. | |
| 8,415,311 B2 | 4/2013 | Manetta et al. | |
| 8,470,788 B2 | 6/2013 | Manetta et al. | |
| 2002/0035076 A1 | 3/2002 | Parks | |
| 2002/0061855 A1 | 5/2002 | Parks | |
| 2007/0116731 A1 | 5/2007 | Astruc et al. | |

FOREIGN PATENT DOCUMENTS

| | | |
|---|---|---|
| FR | 2867684 A1 | 9/2005 |
| WO | 0128555 A1 | 4/2001 |
| WO | 03032976 A1 | 4/2003 |
| WO | 03032977 A1 | 4/2003 |
| WO | 03066009 A1 | 8/2003 |
| WO | 03075656 A2 | 9/2003 |
| WO | 2004093886 A1 | 11/2004 |
| WO | 2005058312 A1 | 6/2005 |
| WO | 2006097628 A1 | 9/2006 |
| WO | 2006131651 A2 | 12/2006 |
| WO | 2006131652 A1 | 12/2006 |
| WO | 2006131653 A1 | 12/2006 |
| WO | 2007071876 A1 | 6/2007 |
| WO | 2007119028 A2 | 10/2007 |
| WO | 2008043973 A1 | 4/2008 |
| WO | 2008043974 A2 | 4/2008 |
| WO | 2010072958 A2 | 7/2010 |
| WO | 2010086725 A1 | 8/2010 |
| WO | 2010092312 A1 | 8/2010 |
| WO | 2014049298 A1 | 4/2014 |

OTHER PUBLICATIONS

Forton "Papulopustular Rosacea, Skin Immunity and Demodex: Pityriasis Folliculorum as a Missing Link"; Journal of te European Academy of Dermatology and Venereology (2012), 26, 19-28.
Finacea (azelaic acid) gel, 15%, label (Jul. 2010).
Holmes, "Potential role of microorganisms in the pathogenesis of rosacea," J Am Acad Dermatol, vol. 69, No. 6, pp. 1025-1032 (2013).
Ianaro et al, "Anti-inflammatory activity of macrolide antibiotics," J Pharmacol Exp Ther, vol. 292, No. 1, pp. 156-163 (2000).
Campbell, "History of avermectin and ivermectin, with notes on the history of other macrocyclic lactone antiparasitic agents," Curr Pharm Biotechnol, vol. 13, No. 6, pp. 853-865 (2012).
Forstinger et al, "Treatment of rosacea-like demodicidosis with oral ivermectin and topical permethrin cream," J Am Acad Dermatol, vol. 41, pp. 775-777 (1999).

(Continued)

*Primary Examiner* — Elli Peselev

(74) *Attorney, Agent, or Firm* — Panitch Schwarze Belisario & Nadel LLP

(57) ABSTRACT

Methods for safe and effective treatment of inflammatory lesions of rosacea in a subject are described. The methods involve once daily topically applying to an affected skin area a topical composition containing ivermectin and a pharmaceutically acceptable carrier. It has been demonstrated that once daily topical treatment with ivermectin is significantly superior than twice-daily topical treatment with metronidazole in reducing inflammatory lesion counts.

19 Claims, 12 Drawing Sheets

(56) References Cited

OTHER PUBLICATIONS

Pariser et al, "Topical 0.5% ivermectin lotion for treatment of head lice," N Engl J Med, vol. 367, No. 18, pp. 1687-1693 (2012).
Zhang et al, "Ivermectin inhibits LPS-induced production of inflammatory cytokines and improves LPS-induced survival in mice," Inflamm Res, vol. 57, pp. 524-529 (2008).
Van Zuuren et al, "Effective and evidence-based management strategies for rosacea: summary of a Cochrane systematic review," Br J Dermatol, vol. 165, No. 4, pp. 760-781 (2011).
Elewski, "Results of a national rosacea patient survey: common issues that concern rosacea sufferers," J Drugs Dermatol, vol. 8, No. 2, pp. 120-123 (2009).
Guzzo et al, "Safety, Tolerability, and Pharmacokinetics of Escalating High Doses of Ivermectin in Healthy Adult Subjects," J. Clin. Pharmacol., vol. 42, pp. 1122-1133 (2002).
Fink et al, "Pharmacokinetics of Ivermectin in Animals and Humans," Ivermectin and Abamectin, Ed. Campbell, Springer-Verlag New York Inc., pp. 113-129 (1989).
Toutain et al, "Plasma terminal half-life," J. Vet. Pharmacol. Therap., vol. 27, pp. 427-439 (2004).
Dahl et al, "Once-daily topical metronidazole cream formulations in the treatment of the papules and pustules of rosacea," J Am. Acad. Dermatol., pp. 723-730 (Nov. 2001).
Thiboutot et al, "Efficacy and safety of azelaic acid (15%) gel as a new treatment for papulopustular rosacea: Results from two vehicle-controlled, randomized phase III studies," J Am Acad Dermatol, vol. 48, No. 6, pp. 836-845 (Jun. 2003).
Canga et al, "The pharmacokinetics and metabolism of ivermectin in domestic animcal species," The Veterinary Journal, vol. 179, No. 1, pp. 25-37 (2009).
Canga et al, "The Pharmacokinetics and Interactions of Ivermectin in Humans—A Mini-review," The AAPS Journal, vol. 10, No. 1, pp. 42-46 (Mar. 2008).
Taib et al. "Superiority of ivermectin 1% cream over metronidazole 0.75% cream in treating inflammatory lesions of rosacea: a randomized, investigator-blinded trial." Br J Dermatol. Sep. 16, 2014.
Allen et al. "Recalcitrant papulopustular rosacea in an immunocompetent patient responding to combination therapy with oral ivermectin and topical permethrin." Cutis. Aug. 2007;80(2):149-51.
Salem et al. "Evaluation of the efficacy of oral ivermectin in comparison with ivermectin-metronidazole combined therapy in the treatment of ocular and skin lesions of *Demodex folliculorum*" International Journal of Infectious Diseases (2013) 17(5), e343-e347.
International Search Report for corresponding PCT/US14/045717 dated Sep. 24, 2014.
International Search Report for corresponding PCT/2014/45739 dated Sep. 24, 2014.
Millikan, The Proposed Inflammatory Pathophysiology of Rosacea: Implications for Treatment; Skinmed. 2003;2(1).
Rebora, "The Management of Rosacea", Am. J. Clin. Dermatol., vol. 3, No. 7, pp. 489-496 (2002).
Gold et al, "Efficacy and safety of ivermectin 1% cream in treatment of papulopustular rosacea: results of two randomized, double-blind, vehicle-controlled pivotal studies," Journal of Drugs in Dermatology, vol. 13, No. 3, pp. 346-323 (Mar. 2014).
Loo et al, "Ivermectin cream in rosacea: comparison with metronidazole gel," British Journal of Dermatology, vol. 151, Supp. 68, p. 61 (2004).
Stankiewicz et al, "Influence of ivermectin on cellular and humoral immune responses of lambs," Veterinary Immunology and Immunopathy, vol. 44, pp. 347-358 (1995).

** p<.001

* p<.01, ** p<.001

* p<.01, ** p<.001

IGA= 4; IL= 63　　　　　　　　　　　IGA= 1; IL= 2

*$p<.05$, **$p<.001$

* $p<.05$, ** $p<.001$

TREATMENT OF INFLAMMATORY LESIONS OF ROSACEA WITH IVERMECTIN

CROSS-REFERENCE TO RELATED APPLICATIONS

This application is entitled to priority pursuant to 35 U.S.C. §119(e) to U.S. Provisional Patent Application No. 61/843,540, filed Jul. 8, 2013, U.S. Provisional Patent Application No. 61/919,208 filed Dec. 20, 2013, and U.S. Provisional Patent Application No. 61/927,717, filed Jan. 15, 2014, the disclosure of each of which is hereby incorporated by reference herein in its entirety.

BACKGROUND OF THE INVENTION

Rosacea is a highly prevalent, chronic inflammatory skin condition estimated to affect 16 million Americans.[1-2] Rosacea is a common, chronic and progressive inflammatory disease with skin features characterized by blushing and flushing, facial erythema, papules, pustules, telangiectasia and sometimes ocular lesions known as ocular rosacea. In severe cases, particularly in men, rhinophyma, or a bulbous enlargement of the nose, may occur. Rosacea develops over the course of several years with periods of exacerbation triggered by various stimuli such as temperature changes, alcohol, spicy foods, sun exposure and emotional factors.

The prevalence of rosacea in the European population ranges between 0.09 and 22%, with a peak age of onset between 25 and 70 and is much more common in people with a light complexion. It more particularly affects women although the condition is generally more severe in men. The prevalence of family histories of rosacea has been reported.

Four subtypes of rosacea have been defined according to the degree of primary features, such as vasomotor flushing, persistent erythema, papules and pustules, telangiectasias (Wilkin J et al., JAAD, 2002, 46: 584-587). Erythematotelangiectatic rosacea (ETR) is mainly characterized by vasomotor flushing and persistent central facial erythema. Telangiectasias are commonly observed but are not essential for the diagnosis of this subtype. Central facial edema, burning or stinging sensations and rough, flaky skin are also symptoms that have sometimes been reported. A history of flushing as the only symptom is commonly found in people with erythematotelangiectatic rosacea.

Papulopustular rosacea (PPR) is characterized by persistent central facial erythema and transient crops of papules and/or pustules in the center of the face. However, the papules and pustules can also occur in periorificial regions, i.e., around the mouth, nose and eyes. The papulopustular subtype resembles acne vulgaris, but comedones are absent. Rosacea and acne may coexist in a same patient, in which case comedones may also be present alongside the papules and pustules suggestive of rosacea. People with papulopustular rosacea sometimes complain of a burning or stinging sensation. This subtype is often observed before or at the same time as ETR (including the presence of telangiectasias). The telangiectasias may be obscured by the persistent erythema and the papules and pustules, but they tend to become more visible after successful treatments that cover up these features. Papulopustular rosacea (PPR) is a subtype of the inflammatory lesions that is associated with great psychological distress.[3] Facial blemishes have been found to significantly impair health-related quality of life, along with a fear of negative evaluation by others.[4] Moreover, PPR is characterized by the presence of inflammatory infiltrates that accompany flares, along with a heightened immune response involving neutrophilic infiltration and increased gene expression of IL-8 (Steinhoff et al. *J Investig Dermatol Symp Proc* 2011; 15:2-11)

Phymatous rosacea is characterized by a thickening of the skin, irregular surface nodularities and swelling. The nose is most commonly affected but phymatous rosacea can also involve other areas such as the chin, the forehead, the cheeks and the ears. Patients with this subtype sometimes exhibit prominent, enlarged follicles in the affected areas as well as telangiectasias. This subtype often occurs before or at the same time as ETR or PPR (including the presence of persistent erythema, telangiectasias, papules and pustules). In the case of rhinophyma, these additional stigmata may be particularly pronounced in the nasal region.

Ocular rosacea (or ophthalmic rosacea) exhibits symptoms restricted to the ocular area with blepharitis, conjunctivitis and keratitis. The diagnosis of ocular rosacea should be considered when a patient presents with one or more of the following ocular signs and symptoms: watery or bloodshot eyes (interpalpebral conjunctival hyperemia), foreign body sensation, burning or stinging, dry or itchy eyes, sensitivity to light, blurred vision, conjunctival telangiectasias or eyelid margin telangiectasias or erythema of the eyelid and periocular area.

The pathogenesis of rosacea is not yet completely understood. Its etiology is multifactorial. In addition to exogenous factors (including UV light, heat and alcohol), it may be secondary to parasitic involvement (particularly *Demodex folliculorum* mites).[5-6] Such factors activate neurovascular and/or immune responses, and consequently inflammatory cascades. Intermittent flares may contribute to the chronicity of rosacea as they are associated with prolonged vasodilation, perivascular inflammation, edema and exposure to cytokines and cellular infiltrates. Some studies of PPR observed higher mite densities compared to controls (Forton et al., *Br J Dermatol* 1993; 128(6):650-9; Karincaoglu et al., *J Dermatol* 2004; 31(8):618-26). Skin affected by rosacea is highly sensitive and prone to iffitation.[7]

Management of rosacea is difficult and currently the most used therapies comprise oral antibiotics (tetracycline or its derivatives, metronidazole and macrolides) and oral retinoids. There are only a few current treatment options for inflammatory lesions of rosacea, and not many alternatives exist with high efficacy and once-daily dosing. A recent Cochrane review noted that it is unclear which is most effective, while some evidence supports the efficacy of topical metronidazole, azelaic acid and subantimicrobial-dose doxycycline in the treatment of moderate to severe rosacea.[8] In a national survey of current rosacea medication users, 46% of patients had previously changed medications, usually due to a lack of improvement.[9] Slow and incomplete treatment, and short period of relapse-free time have been noticed with some conventional treatments.

Ivermectin is an anti-parasitic drug derivative from the macrocyclic lactones family approved for human use for treatment and chemoprophylaxis of onchocerciasis and strongyloidiasis since 1996 in the USA and since 1988 in France. In addition, it has been in approved in France for the treatment of human scabies. Oral ivermectin in human and animal demodicidosis was effective in reducing *Demodex folliculorum* and improving demodicidosis. Moreover, when administered orally, ivermectin combined with a subsequent weekly application of topical permethrin showed treatment efficacy in a patient presenting chronic rosacea-like demodicidosis (14).

U.S. Pat. No. 5,952,372 discloses a method of treating rosacea in humans involving orally or topically administering ivermectin. However, according to U.S. Pat. No. 5,952,372, because of the skin barrier effect, topical treatment with ivermectin would be anticipated to require once- or twice-daily applications for as long as four weeks to achieve sufficient follicle penetration and effective miticidal activity. It further describes that after ivermectin carries out its miticidal activity on skin *Demodex folliculorum* organisms, inflammatory responses to them begin to diminish but remnants of the dead mites still elicit some flushing and lesion formation until the cleanup processes of the body remove them, a process that requires six to eight weeks. It suggests to employ conventional anti-rosacea medications, such as oral tetracycline and topical metronidazole, to suppress early flareups and to give early clinical response during the initial phase of ivermectin administration. U.S. Pat. No. 5,952,372 contains no specific disclosure on topical treatment of PPR.

U.S. Pat. No. 6,133,310 and U.S. Pat. No. 8,415,311 also disclose a method of treating acne rosacea by topical application of ivermectin. However, they contain no specific disclosure on treating inflammatory lesions of rosacea or PPR.

Accordingly, there is a need for an once-daily topical treatment of inflammatory lesions of rosacea with an earlier onset of significant effectiveness and a prolonged time to relapse than the currently available treatments, in order to provide safe, more rapid and longer lasting relief, and better patient compliance to those in need of such treatment. Such need is met by the present invention.

BRIEF SUMMARY OF THE INVENTION

It is now demonstrated that topical administration of 0.5 to 1.5% by weight of ivermectin provided more rapid relief of inflammatory lesions of rosacea as well as longer period of time that is free of relapse as compared to the currently available treatments, such as the topical treatment with 0.75% by weight of metronidazole.

In one general aspect, embodiments of the present invention relate to a method of treating inflammatory lesions of rosacea in a subject in need thereof, comprising topically administering once daily, to a skin area affected by the inflammatory lesions of rosacea a pharmaceutical composition comprising 0.5% to 1.5% by weight ivermectin and a pharmaceutically acceptable carrier, wherein as early as 2 weeks after the initial administration of the pharmaceutical composition, a significant reduction in inflammatory lesion count is observed.

In another general aspect, the present invention relates to a method of treating inflammatory lesions of rosacea in a subject in need thereof, comprising topically administering, once daily, to a skin area affected by the inflammatory lesions a pharmaceutical composition comprising 1% by weight ivermectin and a pharmaceutically acceptable carrier, wherein as early as 2 weeks after the initial administration of the pharmaceutical composition to the subject, a significant reduction in inflammatory lesion count is observed and a steady state of plasma concentration of ivermectin is reached in the subject, wherein the steady state has a mean $C_{max}$ of ivermectin of 2.10±1.04 ng/mL with a range of 0.69-4.02 ng/mL, and a mean $AUC_{0-24\ hr}$ of 36.14±15.56 ng·hr/mL with a range of 13.69-75.16 ng·hr/mL.

In a preferred embodiment of the present invention, the subject has moderate to severe papulopustular rosacea before the treatment.

In another preferred embodiment of the present invention, the subject has at least 10, preferably at least 12 and more preferably at least 15, inflammatory lesions of rosacea, before the treatment.

According to embodiments of the present invention, once daily topical treatment with ivermectin is significantly superior than twice-daily topical treatment with metronidazole in treating inflammatory lesions of rosacea.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise embodiments shown in the drawings.

DETAILED DESCRIPTION OF THE INVENTION

Figure 1:
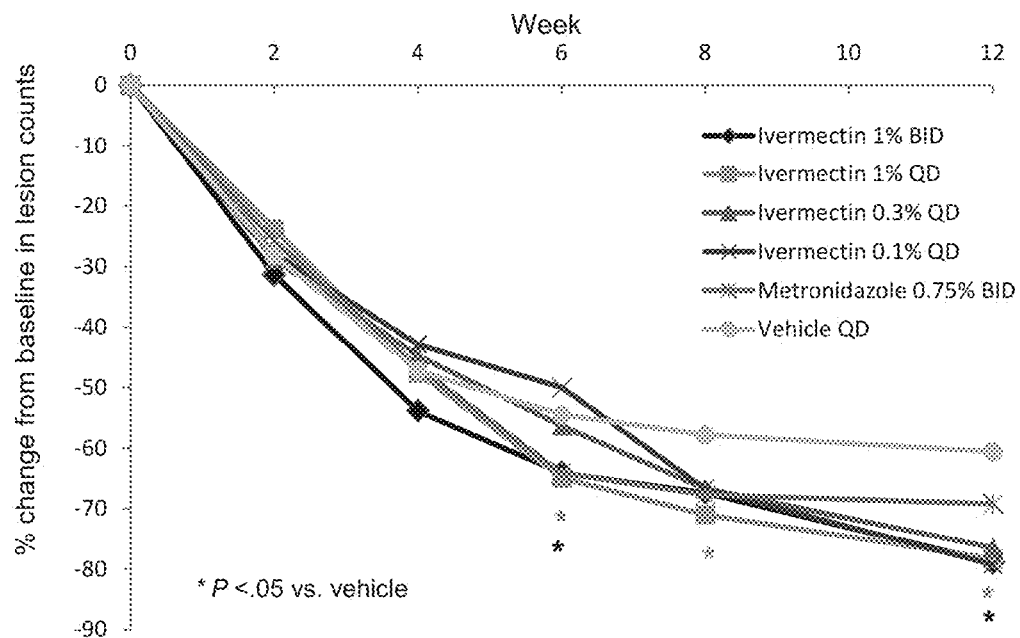
FIG. 1 shows the median percentage change from baseline in lesion counts (ITT-LOCF population) in a dose range study, after various topical treatments.

Various publications, articles and patents are cited or described in the background and throughout the specification; each of these references is herein incorporated by reference in its entirety. Discussion of documents, acts, materials, devices, articles, or the like which have been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural references unless the context clearly dictates otherwise.

Ivermectin is a member of the avermectin class, which has been shown in immunopharmacological studies to exert anti-inflammatory effects by inhibiting lipopolysaccharide-induced production of inflammatory cytokines, such as tumor necrosis factor alpha and interleukin (IL)-1b, while upregulating the anti-inflammatory cytokine IL-10[10]. It is a semisynthetic derivative isolated from the fermentation of *Streptomyces avermitilis*, that belongs to the avermectin family of macrocyclic lactones. Ivermectin is a mixture containing 5-O-demethyl-22,23-dihydroavermectin Ala plus 5-O-demethyl-25-de(1-methylpropyl)-25-(1-methylethyl)-22,23-dihydroavermectin Ala, generally referred to as 22,23-dihydroavermectin B1a and B1b or H2B1a and H2B1b, respectively. The respective empirical formulas of H2B1a and H2B1b are $C_{48}H_{74}O_{14}$ and $C_{47}H_{72}O_{14}$ with molecular weights of 875.10 and 861.07 respectively.

Ivermectin is a macrocyclic lactone derivative, its therapeutic effect is thought to be prominently due to its anti-inflammatory properties, similar to that of other macrolides.[11-12] Avermectin has been reported to exert anti-inflammatory effects by inhibiting lipopolysaccharide-induced production of inflammatory cytokines. In addition to its anti-inflammatory mode of action, ivermectin possesses antiparasitic properties. Its predecessor, avermectin, is an antiparasitic agent of agricultural importance first isolated in 1974.[13] Several studies support ivermectin's role in the effective oral treatment of cutaneous demodicidosis (in combination with topical permethrin cream) and scabies, as well as topical treatment of head lice.[14-16] Ivermectin causes death of parasites, primarily through binding selectively and with high affinity to glutamate-gated chloride channels, which occur in invertebrate nerve and muscle cells. This leads to the interruption of nerve impulses, causing paralysis and death of parasitic organisms. Ivermectin is known to act on *Demodex* mites in localized and generalized demodicidosis in animals and in humans.

In the present invention, studies were conducted to evaluate the efficacy and safety of ivermectin in treating inflammatory lesions of rosacea, such as papulopustular rosacea (PPR).

It was discovered that, as early as 2 weeks after the initial topical administration of a pharmaceutical composition comprising 0.5 to 1.5% (w/w) ivermectin to the subject, a significant reduction in inflammatory, lesion count was observed.

As used herein, a "significant reduction" refers to a reduction that is statistically significant, not due to chance alone, which has a p-value of 0.05 or less. A "significant reduction" can have a p-value of less than 0.05, 0.04, 0.03, 0.01, 0.005, 0.001, etc. As used herein, "inflammatory lesion count" refers to the number of inflammatory lesions associated with rosacea or PPR. Inflammatory lesions can be papules and/or pustules. A papule is a small, solid elevation less than one centimeter in diameter, and a pustule is a small, circumscribed elevation of the skin, which contains yellow-white exudates.

The lesions can be, e.g., papules and/or pustules of any sizes (small or large). For example, at two weeks after the initial treatment, about 30% (p<0.001) and 27.3% (p<0.01) median reduction of the inflammatory lesion counts were observed from patients treated with ivermectin in two separate clinical studies using methods of the present invention. These reductions are statistically significant because they had p values less than 0.01 or even less than 0.001.

This early onset of significant effectiveness is unexpected and surprising in comparison to the conventional treatments. For example, significant treatment differences were only observed from week 4 or week 8 forward in two phase III studies for the topical treatment of moderate PPR using twice-daily 15% azelaic acid (Thiboutot et al., 2003, *J. Am Acad Dermatol*, 48 (6): 836-845), while no statistically significant difference with respect to the median inflammatory lesion counts or the median percentage change in inflammatory lesion counts was observed at any evaluation time during the study (P≥0.29) of topical treatment of moderate to severe PPR using once-daily 0.75% or 1.0% metronidazole (Dahl et al., 2001, *J. Am Acad Dermatol*, 45 (5): 723-730).

This early onset of significant effectiveness is also unexpected and surprising in view of the prior teaching that topical treatment with ivermectin would be anticipated to require once- or twice-daily applications for as long as four weeks to achieve sufficient follicle penetration and effective miticidal activity; and that after ivermectin carries out its miticidal activity on skin *Demodex folliculorum* organisms, remnants of the dead mites still elicit some flushing and lesion formation until the cleanup processes of the body remove them, a process that requires six to eight weeks; and that conventional anti-rosacea medications, such as oral tetracycline and topical metronidazole, are suggested to be employed to suppress early flareups and to give early clinical response during the initial phase of ivermectin administration (see, e.g., U.S. Pat. No. 5,952,372).

In addition, it was discovered in the present invention that after repeated topical administration of a pharmaceutical composition comprising 0.5 to 1.5% (w/w) ivermectin and a pharmaceutically acceptable carrier, plasma concentrations of ivermectin increased progressively until reaching a plateau or steady state. It was also observed that the repeated topical administration results in a much longer terminal half-life of ivermectin in the subject than that for orally administered ivermectin, indicating that the rate limiting step in the decrease of plasma ivermectin concentration is the slow and constant release of ivermectin from the administration site on skin into the blood, rather than the rate of eliminating ivermectin from the blood, i.e., a "flip flop" phenomenon (Toutain et al, 2004, *J. Vet. Pharmacal. Therap*. 27: 427-439). Surprisingly, despite this rate-limiting factor of slow and constant release of ivermectin from the skin into the blood, no further systemic accumulation of ivermectin was observed after prolonged topical treatment with 0.5 to 1.5% (w/w) ivermectin. Thus, a topical treatment according to an embodiment of the present invention is safe and can be conducted for as long as it is needed without causing any safety concerns.

Side-by-side clinical studies in the present invention also showed that methods according to embodiments of the present invention result in more reduction in inflammatory lesion counts as well as longer time for the relapse of inflammatory lesions to occur than the conventional topical treatment, such as that with metronidazole. In addition, methods according to embodiments of the present invention also result in less frequent adverse skin reactions than the conventional topical treatments.

While not wishing to be bound by the theory, it is believed that the mechanism of action of ivermectin in treating inflammatory lesions of rosacea may be linked to anti-inflammatory effects of ivermectin as well as the death of *Demodex* mites that have been reported to be a factor in inflammation of the skin. Because ivermectin has both anti-inflammatory and anti-parasitic activities, treatment of inflammatory lesions with ivermectin represents an innovative therapy addressing these relevant pathogenic factors in rosacea, thus a novel addition to the current treatment armamentarium.

According to an embodiment of the present invention, a method of treating inflammatory lesions of rosacea in a subject in need thereof, comprises topically administering, once daily, to a skin area affected by the inflammatory lesions of rosacea a pharmaceutical composition comprising 0.5% to 1.5% by weight ivermectin and a pharmaceutically acceptable carrier, wherein as early as 2 weeks after the initial administration of the pharmaceutical composition, a significant reduction in inflammatory lesion count is observed.

As used herein, "pharmaceutically acceptable carrier" refers to a pharmaceutically acceptable vehicle or diluent comprising excipients and auxiliaries that facilitate processing of the active compounds into preparations which can be used pharmaceutically.

The pharmaceutical compositions according to the invention are suited for treating the skin. They can be in liquid, pasty or solid form, and more particularly in the form of ointments, creams, milks, pomades, powders, impregnated pads, syndets, towelettes, solutions, gels, sprays, foams, suspensions, lotions, sticks, shampoos or washing bases. They can also be in the form of suspensions of microspheres or nanospheres or of lipid or polymeric vesicles or of polymeric patches and of hydrogels for controlled release. These compositions for topical application can be in anhydrous form, in aqueous form, or in the form of an emulsion.

In one embodiment of the present invention, the pharmaceutical composition being formulated as an emulsion, the topical pharmaceutical emulsion comprises ivermectin, and one or more other ingredients selected from the group consisting of: an oily phase comprising dimethicone, cyclomethicone, isopropyl palmitate and/or isopropyl myristate, the oily phase further comprising fatty substances selected from the group consisting of cetyl alcohol, cetostearyl alcohol, stearyl alcohol, palmitostearic acid, stearic acid and self-emulsifiable wax; at least one surfactant-emulsifier selected from the group consisting of glyceryl/PEG100 stearate, sorbitan monostearate, sorbitan palmitate, Steareth-20, Steareth-2, Steareth-21 and Ceteareth-20; a mixture of solvents and/or propenetrating agents selected from the group consisting of propylene glycol, oleyl alcohol, phenoxyethanol and glyceryl triacetate; one or more gelling agents selected from the group consisting of carbomers, cellulose gelling agents, xanthan gums, aluminum magnesium silicates but excluding aluminum magnesium silicate/titanium dioxide/silica, guar gums, polyacrylamides and modified starches; and water.

In a preferred embodiment of the present invention, the pharmaceutical composition comprises about 1% (w/w) ivermectin, and a pharmaceutically acceptable carrier.

In another preferred embodiment of the present invention, the pharmaceutical composition comprises about 1% (w/w) ivermectin, and one or more inactive ingredients selected from the group consisting of carbomer, such as carbomer copolymer type B; cetyl alcohol; citric acid monohydrate; dimethicone 20 Cst; edetate disodium; glycerin; isopropyl palmitate; methyl paraben; oleyl alcohol; phenoxyethanol; polyoxyl 20 cetostearyl ether; propylene glycol; propyl paraben; purified water; sodium hydroxide; sorbitan monostearate and stearyl alcohol.

As used herein, the term "subject" means any animal, preferably a mammal, most preferably a human, to whom will be or has been administered compounds or topical formulations according to embodiments of the invention. Preferably, a subject is in need of, or has been the object of observation or experiment of, treatment or prevention of inflammatory lesions of rosacea or papulopustular rosacea.

As known to those skilled in the art, an "intent-to-treat population" or "ITT population" refers to all subjects who are randomized in a clinical study and to whom the study drug is administered. "ITT-LOCF" refers to the ITT population using the Last Observation Carried Forward (LOCF) method, a standard method of handling missing data that imputes or fills in values based on existing data. "ITT-MI" refers to the ITT population using the multiple imputations (MI) method based on all the data available in the model, another method for processing data known to those skilled in the art. A "per protocol population" or "PP population" refers to subjects of the ITT population in a clinical study who have no major deviations from the protocol of study.

As used herein, the term "inflammatory lesions of rosacea" include any type of skin lesions associated with the inflammatory phase of rosacea. Examples of "inflammatory lesions of rosacea" include various sizes of papules and pustules associated with rosacea. In a preferred embodiment of the present invention, the inflammatory lesions of rosacea comprise inflammatory lesions of papulopustular rosacea (PPR), more preferably inflammatory lesions of moderate to severe PPR.

In one embodiment, "treatment" or "treating" refers to an amelioration, prophylaxis, or reversal of a disease or disorder, or of at least one discernible symptom thereof. In another embodiment, "treatment" or "treating" refers to an amelioration, prophylaxis, or reversal of at least one measurable physical parameter related to the disease or disorder being treated, not necessarily discernible in or by the mammal. In yet another embodiment, "treatment" or "treating" refers to inhibiting or slowing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

Success of treating inflammatory lesions of rosacea or PPR can be measured using methods known in the art, such as by the reduction of inflammatory lesion count from the baseline before treatment, by an improvement from the baseline in an investigator's global assessment (IGA) score, or by both the reduction of inflammatory lesion count and the IGA score.

The IGA score is determined by a trained medical professional evaluating the skin condition of a patient utilizing an investigative global assessment of the skin condition. Typically, such global assessments assign a value to the degree of rosacea exhibited by the skin. In addition to the assessment made by the medical professional, the patient's input and observations of their skin condition and responses to various inquiries (e.g., stinging or burning sensations) also play a role in determining the IGA score that is assigned. For example, the IGA score for rosacea (Table 1) can, range, for example, from 0 (clear) to 1 (almost clear) to 2 (mild) to 3 (moderate) to 4 (Severe), including values between these numeric gradings, such as 1.5, 2.6, 3.4 etc. (e.g., intervals of 0.1).

TABLE 1

Investigator's Global Assessment of Rosacea Severity

| Grade | Score | Clinical Description |
|---|---|---|
| Clear | 0 | No inflammatory lesions present, no erythema |
| Almost Clear | 1 | Very few small papules/pustules, very mild erythema present |
| Mild | 2 | Few small papules/pustules, mild erythema |
| Moderate | 3 | Several small or large papules/pustules, moderate erythema |
| Severe | 4 | Numerous small and/or large papules/pustules, severe erythema |

In view of the present disclosure, a skin area that is affected by inflammatory lesions of rosacea or papulopustular rosacea can be identified using any diagnostic signs or means known in the art, and can be treated by methods according to embodiments of the present invention. Patients can have papulopustular rosacea at different stages, from mild to severe.

In a preferred embodiment, the patient has moderate to severe papulopustular rosacea. As used herein, a patient having "moderate to severe papulopustular rosacea" has at least moderate facial erythema and at least 10 papulopustular lesions before treatment. For example, the patient can have an IGA of rosacea of 3 or 4, and at least 10, 12, 15, 20, 25 or more papulopustular lesions before treatment.

According to embodiments of the present invention, the inflammatory lesions of rosacea or papulopustular rosacea is treated by topically applying to an affected skin area a pharmaceutical composition comprising ivermectin and a pharmaceutically acceptable carrier, and the treatment results in a reduction in the inflammatory lesion count of rosacea from the baseline number of lesions (before treatment) by at least 1 to 100 lesions or more, such as at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 50, 60, 70, 80, 90 or 100 lesions or more. According to embodiments of the present invention, at least about 10%, 20%, 30%, 40%, 50%, 60%, 70%, 80%, 90% or 100% reduction in inflammatory lesion count is observed after the treatment. Depending on the number of inflammatory lesions, and other factors, such as the conditions of the patient, the treatment can last as long as it is needed, such as 4 to 12 weeks.

According to other embodiments of the present invention, the treatment reduces the IGA score in the treated subject. As used herein, the "success rate" in a clinical study refers to the percentage of subjects in the study having an IGA of 0 ("clear") or 1 ("almost clear") after the treatment.

According to embodiments of the present invention, after the initial successful treatment with ivermectin, i.e., to an IGA of 0 or 1, it takes a longer time to relapse, i.e., to an IGA of 2 or above, as compared to the conventional treatments, such as topical treatment with 0.75% by weight metronidazole. For example, treatment with ivermectin (1%) once daily (QD) resulted in a statistically significant extended remission (e.g., delayed time to first relapse, and increase in the number of treatment free days) of rosacea when compared to metronidazole 0.75% BID in subjects who were successfully treated (IGA 0 or 1) for 16 weeks. There was also a numerical trend in favor of ivermectin 1% QD for the relapse rates.

As used herein, "time to first relapse" is defined as the time elapsed between initial successful treatment to an IGA of rosacea of 0 or 1 to the first reoccurrence of the IGA to 2 or more in a subject. According to embodiments of the present invention, the median time to first relapse is about 110, 115, 120, 125, 130, 135, 140, 145 or 150 days or more in subjects treated with ivermectin, with a p value of 0.05 or less.

Another aspect of the present invention relates to a method of treating papulopustular rosacea in a subject in need thereof, comprising topically administering, once daily, to a skin area affected by the papulopustular rosacea a pharmaceutical composition comprising 1% by weight ivermectin and a pharmaceutically acceptable carrier, wherein as early as 2 weeks after the initial administration of the pharmaceutical composition to the subject, a significant reduction in inflammatory lesion count is observed.

Preferably the subject has moderate to severe PPR. More preferably, the subject has at least 15 inflammatory lesions of PPR before the treatment.

In another preferred embodiment, at two weeks after the initial treatment, about 27% or more median reduction of the inflammatory lesion counts is observed from subjects treated with ivermectin, with a p value of 0.01 or less.

In an embodiment of the present invention, as early as 2 weeks after the initial administration of the pharmaceutical composition to the subject, more reduction in the inflammatory lesion count in the subject is observed as compared with a vehicle control. In other embodiments of the present invention, the method results in more reduction of the inflammatory lesion count in the subject in comparison to that achieved by topically administering to the subject a second pharmaceutical composition comprising 0.75% by weight metronidazole.

According to an embodiment of the present invention, a steady state of plasma concentrations of ivermectin is reached in the subject after repeated administration. For example, after about two weeks of once daily topical administration of a pharmaceutical composition containing about 1% (w/w) ivermectin, a steady state of plasma concentration of ivermectin is reached. At this steady state, a mean $C_{max}$, i.e., the highest mean (±standard deviation) plasma concentration of ivermectin, peaked within 10±8 hours post-dose, is 2.10±1.04 ng/mL (range: 0.69-4.02 ng/mL), and a highest mean (±standard deviation) $AUC_{0-24\ hr}$ is 36.14±15.56 ng·hr/mL (range: 13.69-75.16 ng·hr/mL). These levels obtained under steady-state conditions are lower than those observed following oral administration of ivermectin.

According to an embodiment of the present invention, at the steady state, the $C_{max}$ of ivermectin ranges from about 0.5 to 10 ng/mL and the $AUC_{0-24\ hr}$ ranges from about 10 to 100 ng·hr/mL in the subject.

According to another embodiment of the present invention, the topical administration of the pharmaceutical composition to the subject results in a mean terminal half-life of ivermectin in the subject that is much longer than that from orally administered ivermectin. In an embodiment of the present invention, the topical administration of the pharmaceutical composition to the subject results in a mean terminal half-life of ivermectin in the subject of about 145 hours in the subject.

In an embodiment of the present invention, a method of treating inflammatory lesions of rosacea in a subject in need thereof, comprises topically administering, once daily, to a skin area affected by the inflammatory lesions a pharmaceutical composition comprising 1% by weight ivermectin and a pharmaceutically acceptable carrier, wherein as early as 2 weeks after the initial administration of the pharmaceutical composition to the subject, a significant reduction in inflammatory lesion count is observed and a steady state of plasma concentration of ivermectin is reached in the subject, and the steady state has a mean $C_{max}$ of ivermectin of 2.10±1.04 ng/mL with a range of 0.69-4.02 ng/mL, and a mean $AUC_{0-24\ hr}$ of 36.14±15.56 ng·hr/mL with a range of 13.69-75.16 ng·hr/mL.

This invention will be better understood by reference to the non-limiting examples that follow, but those skilled in the art will readily appreciate that the examples are only illustrative of the invention and the claims which follow thereafter.

Unless otherwise indicated, all percentages of the ingredients in the present application are percentages by weight (w/w).

Example 1

Topical Ivermectin Compositions

Examples of pharmaceutical compositions that can be used in the present invention are described in U.S. Pat. No. 8,415,311 and U.S. Pat. No. 8,470,788, which are incorporated herein by reference. Compositions useful in the present invention include, but are not limited to, the following:

| Composition 1 | |
|---|---|
| Ingredients | % by weight relative to the total weight of the Composition |
| Ivermectin | 1.00 |
| Glycerol | 4.0 |
| Aluminum magnesium silicate | 1.0 |
| Methyl para-hydroxybenzoate | 0.2 |
| Disodium EDTA | 0.05 |
| Citric acid monohydrate | 0.05 |
| Isopropyl palmitate | 4.0 |
| Glyceryl/PEG 100 stearate | 3.0 |
| Self-emulsifiable wax | 2.0 |
| Palmitostearic acid | 2.5 |
| Steareth-20 | 3.0 |
| Sorbitan stearate | 2.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

| Composition 2 | |
|---|---|
| Ingredients | % by weight relative to the total weight of the composition |
| Ivermectin | 1.00 |
| Glycerol | 4.0 |
| Acrylate C10-30 alkyl acrylate Crosspolymer | 0.15 |
| Methyl para-hydroxybenzoate | 0.2 |
| Disodium EDTA | 0.05 |
| Citric acid monohydrate | 0.05 |
| Isopropyl myristate | 4.0 |
| Cetyl alcohol | 3.0 |
| Stearyl alcohol | 2.0 |
| Self-emulsifiable wax | 0.8 |
| Palmitostearic acid | 0.5 |
| Steareth-20 | 2.0 |
| Sorbitan palmitate | 1.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

| Composition 3 | |
|---|---|
| Ingredients | % by weight relative to the total weight of the composition |
| Ivermectin | 1.00 |
| Glycerol | 4.0 |
| Aluminum magnesium silicate | 1.0 |
| Methyl para-hydroxybenzoate | 0.2 |
| Disodium EDTA | 0.05 |
| Citric acid monohydrate | 0.05 |
| Isopropyl palmitate | 4.0 |
| Glyceryl/PEG 100 stearate | 3.0 |
| Self-emulsifiable wax | 2.0 |
| Palmitostearic acid | 3.0 |
| Steareth-20 | 3.0 |
| Sorbitan palmitate | 2.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

| Composition 4 | |
|---|---|
| Ingredients | % by weight relative to the total weight of the composition |
| Ivermectin | 1.00 |
| Glycerol | 4.0 |
| Acrylate C10-30 alkyl acrylate Crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH |
| Water | qs 100 |

| Composition 5 | |
|---|---|
| Ingredients | % by weight relative to the total weight of the composition |
| Ivermectin | 1.4 |
| Glycerol | 4.0 |
| Acrylate C10-30 alkyl acrylate Crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |

-continued

Composition 5

| Ingredients | % by weight relative to the total weight of the composition |
|---|---|
| Propyl para-hydroxybenzoate | 0.1 |
| Propylene glycol | 2.0 |
| Phenoxyethanol | 1.0 |
| 10% sodium hydroxide | qs pH |
| Water | qs 100 |

Example 2

Dosage Study on Topical Treatment of PPR with Ivermectin

A phase II, randomized, investigator-blinded, parallel-group, active- and vehicle-controlled study was conducted to determine the optimal concentration and dose regimen of topical ivermectin cream for the treatment of inflammatory lesions of rosacea, and evaluate efficacy and safety.

Eligible subjects were adults with PPR. The majority of the subjects had at least 15 facial inflammatory lesions and at least mild facial erythema based on IGA of rosacea severity. Table 2 shows the demographic and baseline clinical characteristics (ITT population) of the subjects telangiectasia [from 0 (none) to 3 (severe)], adverse events, and satisfaction questionnaire (at the end of the study) were determined during the study.

FIG. 1 shows the median percentage change from baseline in lesion counts (ITT-LOCF population).

At week 12, both ivermectin 1% (w/w) QD and BID were significantly more effective than vehicle QD in the ITT-LOCF analysis based on the percentage change from baseline in inflammatory lesion counts (median: −78.3% and −78.9% vs. −60.6%; both p<0.05) (FIG. 1); this was also confirmed in the PP analysis. Although ivermectin 1% (w/w) BID was significantly more efficacious than vehicle, its magnitude of effect was not greater than ivermectin 1% (w/w) QD. A numeric trend favoring ivermectin 1% QD compared with metronidazole 0.75% BID was also observed in terms of median % change from baseline in inflammatory lesion counts [−78.3% vs. −69.2% at Week 12 (ITT-LOCF)] the sample size was not large enough to detect differences between these groups.

All ivermectin dose regimens led to a significantly greater success rate than vehicle (70.8%, 65.4%, 63.8% and 62.7% for ivermectin 1% BID, 1% QD, 0.3% QD and 0.1% QD, respectively, vs. 42.0% for vehicle at Week 12; all p<0.05). Furthermore, the success rate for Metronidazole was 62.5%. No difference was observed in the change in erythema or telangiectasia between the active and control groups.

All regimens were safe and well-tolerated, with similarly low incidence of adverse events. There were no serious

TABLE 2

|  | Ivermectin 1% BID (N = 48) | Ivermectin 1% QD (N = 52) | Ivermectin 0.3% (N = 47) | Ivermectin 0.1% (N = 51) | Metronidazole 0.75% BID (N = 48) | Vehicle QD (N = 50) |
|---|---|---|---|---|---|---|
| Gender, n (%) |  |  |  |  |  |  |
| Female | 39 (81.3) | 33 (63.5) | 29 (61.7) | 31 (60.8) | 34 (70.8) | 35 (70.0) |
| Male | 9 (18.8) | 19 (36.5) | 18 (38.3) | 20 (39.2) | 14 (29.2) | 15 (30.0) |
| Age, year |  |  |  |  |  |  |
| Mean ± SD | 50.9 ± 12.3 | 50.4 ± 14.5 | 53.4 ± 14.5 | 52.7 ± 13.8 | 52.2 ± 15.9 | 52.2 ± 14.4 |
| Phototype, n (%) |  |  |  |  |  |  |
| I | 7 (14.6) | 4 (7.7) | 6 (12.8) | 4 (7.8) | 3 (6.3) | 7 (14.0) |
| II | 28 (58.3) | 27 (51.9) | 20 (42.5) | 26 (51.0) | 29 (60.4) | 28 (56.0) |
| III | 12 (25.0) | 14 (26.9) | 17 (36.2) | 18 (35.3) | 14 (29.2) | 15 (30.0) |
| IV | 1 (2.1) | 7 (13.5) | 4 (8.5) | 3 (5.9) | 2 (4.1) | 0 |
| Inflammatory lesion, n (%) |  |  |  |  |  |  |
| Mean ± SD | 37.3 ± 39.0 | 35.8 ± 18.2 | 35.1 ± 20.5 | 31.1 ± 15.0 | 37.4 ± 23.9 | 35.8 ± 19.9 |
| Min, max | 16, 270 | 16, 93 | 14, 108 | 15, 79 | 15, 153 | 15, 120 |
| IGA, n (%) |  |  |  |  |  |  |
| 1 = Almost Clear | 2 (4.2) | 0 | 1 (2.1) | 1 (2.0) | 1 (2.1) | 1 (2.0) |
| 2 = Mild | 15 (31.3) | 20 (38.5) | 15 (31.9) | 18 (35.3) | 18 (37.5) | 12 (24.0) |
| 3 = Moderate | 28 (58.3) | 24 (46.2) | 21 (44.7) | 29 (56.9) | 21 (43.8) | 28 (56.0) |
| 4 = Severe | 3 (6.3) | 8 (15.4) | 10 (21.3) | 3 (5.9) | 8 (16.7) | 9 (18.0) |

The subjects were randomized to receive one of the following six (6) regimens for 12 weeks: ivermectin 0.1% (w/w) once-daily (QD), ivermectin 0.3% (w/w) QD, ivermectin 1% (w/w) QD, ivermectin 1% (w/w) twice-daily (BID), metronidazole gel 0.75% (w/w) BID, or vehicle QD. The 6 groups were comparable in terms of demographic and baseline disease characteristics (Table 1): majority were female, Caucasian, with a skin phototype II and a mean age of 51.9±14.2 years. On average, the subjects had 35.4±23.8 inflammatory lesions, and the majority (51.0%) had an IGA of 3 (moderate).

Inflammatory lesion (sum of papules and pustules) counts, rate of success [% subjects "clear" or "almost clear" based on Investigator's Global Assessment (IGA), a scale from 0 (clear) to 4 (severe)], erythema [from 0 (none) to 3 (severe)], related AEs. The majority of related AEs were mild, transient and dermatologic in nature, the most frequent for the ivermectin groups being skin discomfort (4 subjects), skin burning sensation (4 subjects), and worsening of rosacea (3 subjects).

Figure 2:
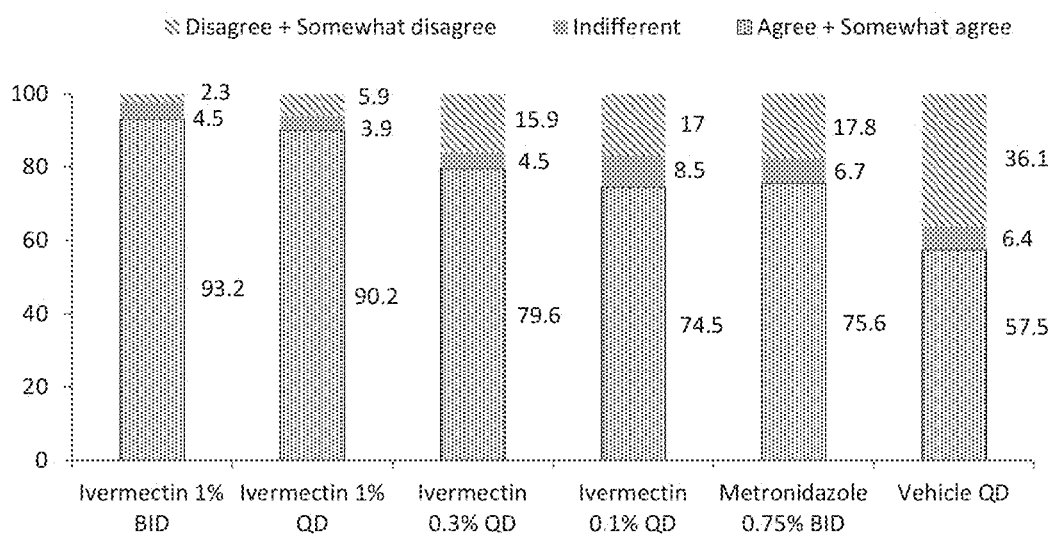
FIG. 2 illustrates subjects' response to the statement "the product improves my rosacea" after various topical treatments (ITT Observed)

FIG. 2 illustrates subjects' response to the statement "the product improves my rosacea" (ITT Observed). With increasing dosage of ivermectin, more subjects agreed with the statement "the product improves my rosacea" (FIG. 2) and were satisfied with the product (data not shown). The result was superior in ivermectin 1% QD and BID groups compared to the metronidazole 0.75% BID group. The majority of subjects in all Ivermectin groups considered that the product was easy to use (at least 95.5%), pleasant to use (at least 77.3%), and did not irritate the skin (at least 70.2%).

Topical administration of all tested ivermectin dose regimens (1% BID, 1% QD, 0.3% QD and 0.1% QD) led to a significantly greater success rate in treating PPR than vehicle; the result was superior in ivermectin 1% QD and BID groups compared to the metronidazole 0.75% BID group; and once daily topical administration of 1% (w/w) ivermectin was considered the optimal dose regimen, because it was safe, well tolerated, and provided significantly greater efficacy than vehicle for the treatment of PPR. Once daily topical administration is further preferred because it promotes better patient compliance.

Example 3

Efficacy and Safety Study of Ivermectin 1% Cream

To demonstrate the efficacy and safety of once-daily ivermectin 1% (w/w) cream in subjects with PPR, two identically designed randomized, double-blind, controlled studies were conducted (hereafter designated Study 1 and Study 2). Both studies were conducted in accordance with the ethical principles of the Declaration of Helsinki and Good Clinical Practices, and in compliance with local regulatory requirements.

Each study had three parts. In the first part of the study, subjects with PPR were treated with ivermectin 1% cream (IVM 1%) or vehicle once daily at bedtime for 12 weeks. In the second part of the study, subjects initially treated with IVM 1% once daily at bedtime continued the same treatment, while subjects treated with the vehicle once daily switched to topical treatment with azelaic acid 15% gel twice daily, in the morning and evening. The third part of the study consisted of 4 weeks safety follow-up, without treatment.

Figure 3:
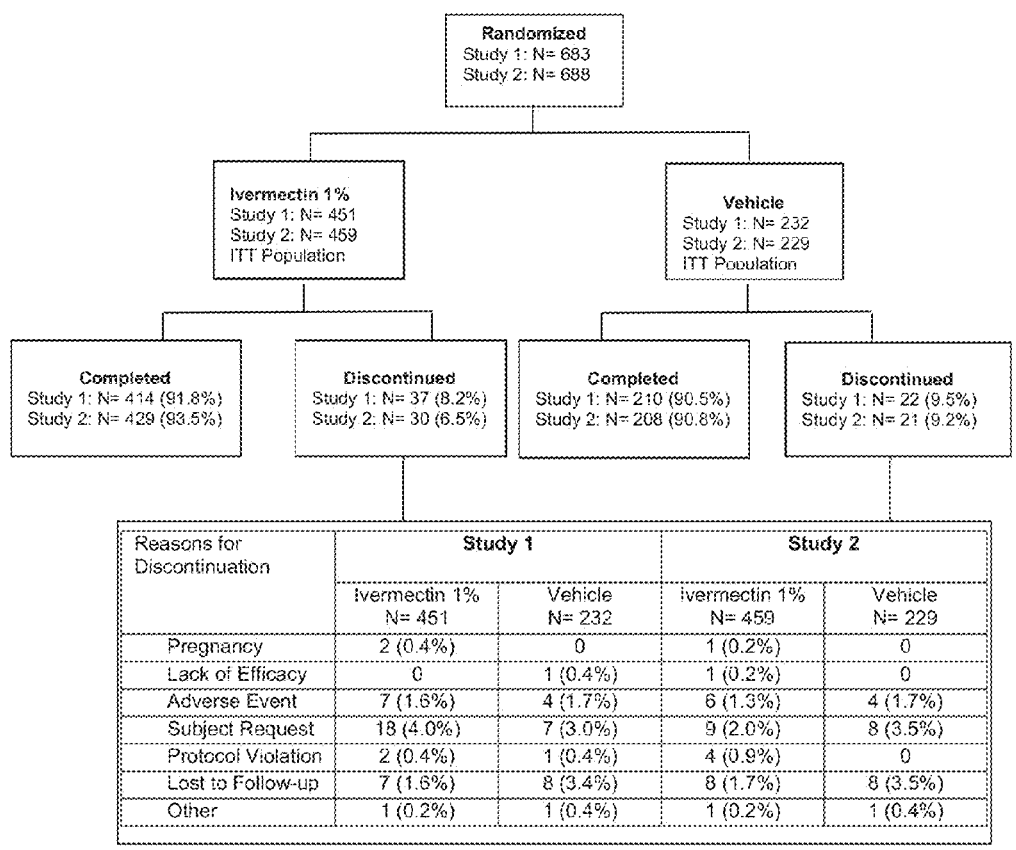
FIG. 3 shows subject disposition in 2 clinical studies on the safety and efficacy of ivermectin topical treatment.

Eligible subjects were 18 years or older, with moderate or severe papulopustular rosacea as noted by an IGA of 3 ("several small or large papules/pustules, moderate erythema") or 4 ("numerous small and/or large papules/pustules, severe erythema"), and presenting with 15-70 facial inflammatory lesions (papules and pustules). A total of 683 subjects with moderate to severe PPR were randomized in Study 1 (IVM 1%: 451, vehicle: 232), and 688 subjects in Study 2 (IVM 1%: 459, vehicle: 229) (FIG. 3).

Eligible subjects received either ivermectin cream 1% cream (once daily every day at bedtime) or vehicle cream (once daily every day at bedtime) on the entire face for 12 weeks. They were instructed to apply a thin film of cream on the entire face (right and left cheeks, forehead, chin and nose), e.g., in a pea-size amount of the cream, avoiding the upper and lower eyelids, lips, eyes and mouth. Subjects were also instructed to avoid rosacea triggers, such as sudden exposure to heat, certain foods, and excessive sun exposure. Study visits during the first study were as follows: screening visits, baseline, weeks 2, 4, 8, and 12 after the initial administration.

Efficacy assessments at each visit were the IGA of disease severity, and inflammatory lesion counts (papules and pustules) on each of the five facial regions (forehead, chin, nose, right cheek, left cheek). Safety assessments included adverse events (AEs) throughout the study, local tolerance parameters (stinging/burning, dryness, itching) at each study visit evaluated on a 4-point scale [from 0 (none) to 3 (severe)], and laboratory parameters (hematology and biochemistry) measured before and after treatment. Other assessments included the subject's evaluation of their rosacea improvement at the end of the study (week 12) compared to their condition at baseline, and two quality of life (QoL) questionnaires [a dermatology-specific instrument, the Dermatology Life Quality Index (DLQI)],[17] and a rosacea-specific instrument, the RosaQoL™[18] completed at baseline and week 12.

The co-primary efficacy endpoints in both studies were the success rate based on the IGA outcome and absolute change from baseline in inflammatory lesion counts at the end of week 12 of the studies. The success rate based on IGA score [% of subjects who achieved "clear" or "almost clear" ratings on the IGA scale at week 12 (ITT-LOCF)] was analyzed by the Cochran-Mantel-Haenszel (CMH) test stratified by analysis site, using the general association statistic. The absolute change in inflammatory lesion counts from baseline to week 12 (ITT-LOCF) was analyzed by analysis of covariance (ANCOVA). Missing data at week 12 in the ITT population were imputed by the LOCF approach. Also, sensitivity analyses were conducted to impute missing data in order to assess the robustness of the primary efficacy results. The secondary efficacy endpoint was percent change in inflammatory lesion counts from baseline at week 12 (ITT-LOCF). The QoL questionnaires were analyzed using the Wilcoxon rank sum test, and other variables were descriptively analyzed. High mean scores from the QoL questionnaires indicated a low quality of life.

In Studies 1 and 2, the vast majority of subjects completed the study (91.4% and 92.6%, respectively). The treatment groups were similar at baseline in terms of demographics and baseline disease characteristics, with about 31-33 inflammatory lesions on average and the majority having moderate rosacea (Table 3). Most subjects were female (68.2% and 66.7% in Studies 1 and 2, respectively) and Caucasian/white (96.2% and 95.3%), with a mean age of 50.4 and 50.2 years, respectively. Additionally, treatment groups were comparable regarding rates/reasons for early study discontinuation (FIG. 3).

TABLE 3

Demographic and baseline clinical characteristics (ITT population)

| | | Study 1 Total (n = 683) | Study 2 Total (n = 688) |
|---|---|---|---|
| Age, years | Mean ± SD | 50.4 ± 12.09 | 50.2 ± 12.29 |
| | Min, Max | 19, 88 | 18, 89 |
| Gender, n (%) | Female | 466 (68.2%) | 459 (66.7%) |
| | Male | 217 (31.8%) | 229 (33.3%) |
| Race | White | 657 (96.2%) | 656 (95.3%) |
| | Black of African American | 9 (1.3%) | 10 (1.5%) |
| | Asian | 6 (0.9%) | 15 (2.2%) |
| | Other | 11 (1.6%) | 7 (1.0%) |
| Inflammatory lesion counts | Mean ± SD | 30.9 ± 14.33 | 32.9 ± 13.70 |
| IGA | 3 = Moderate | 560 (82.0%) | 403 (83.3%) |
| | 4 = Severe | 123 (18.0%) | 81 (16.7%) |

Figure 4A:
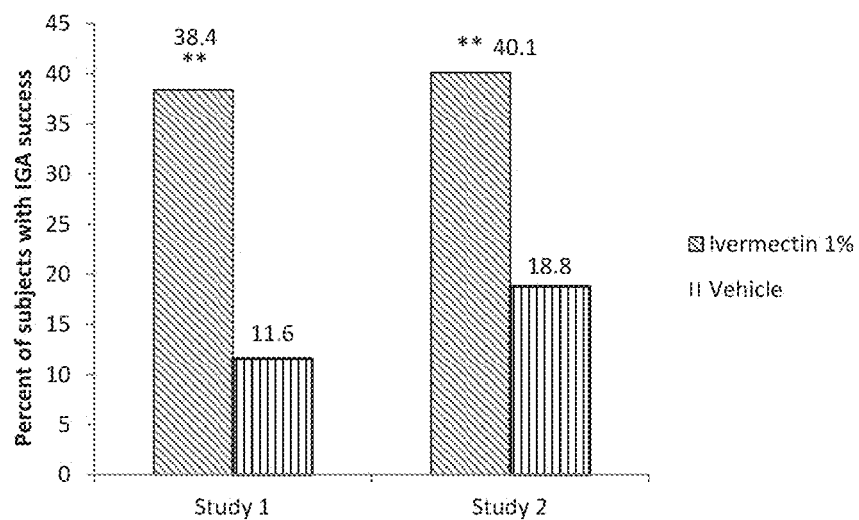
FIG. 4 illustrates proportions of subjects achieving IGA success ("clear" or "almost clear"): (A) at week 12 in studies 1 and 2; (B) at weeks 2, 4, 8 and 12 in study 1; and (C)) at weeks 2, 4, 8 and 12 in study 2, wherein SOOLANTRA is a 1% ivermectin cream.
Figure 4B:
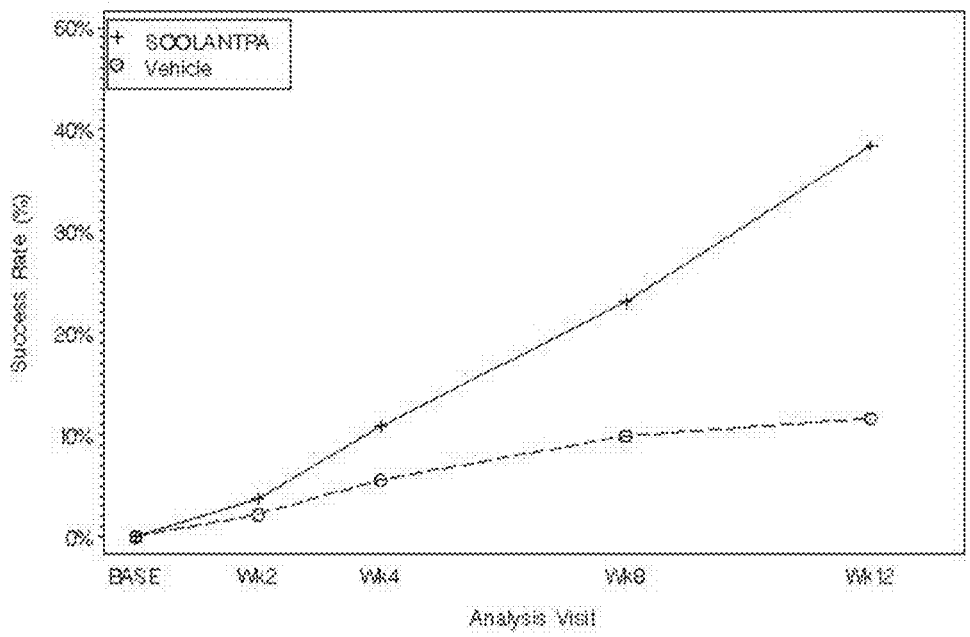
Figure 4C:
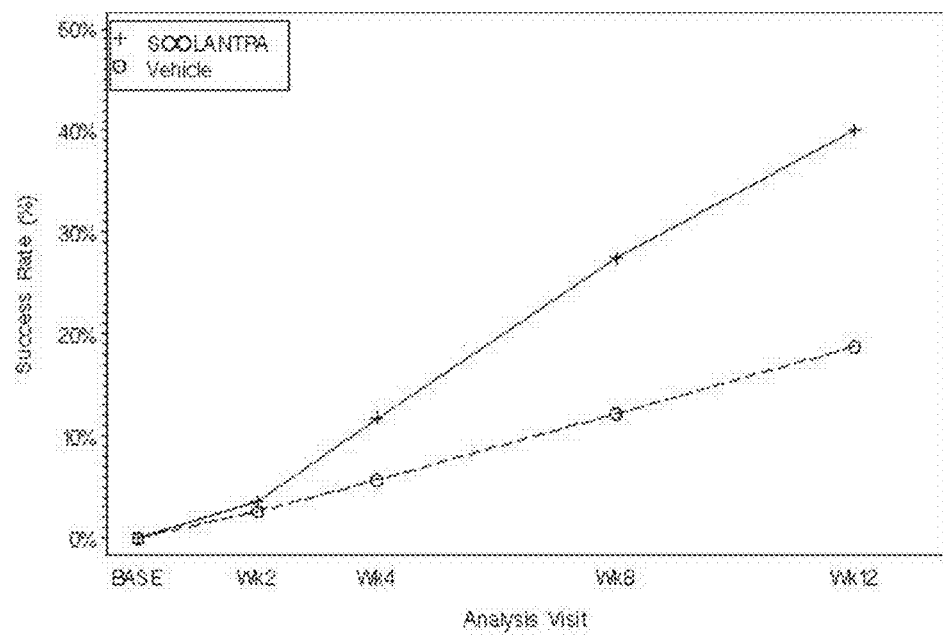

The proportion of subjects achieving IGA success ("clear" or "almost clear") at week 12 for Studies 1 and 2 were 38.4% and 40.1%, respectively for IVM 1% compared to 11.6% and 18.8% for vehicle (both p<0.001; FIG. 4A). A significant difference between treatment arms in both studies was observed based on IGA since week 4 (10.9% and 11.8% versus 5.6% and 5.7%, respectively; both p<0.05), and was sustained until Week 12 (FIGS. 4B and 4C).

Figure 5A:
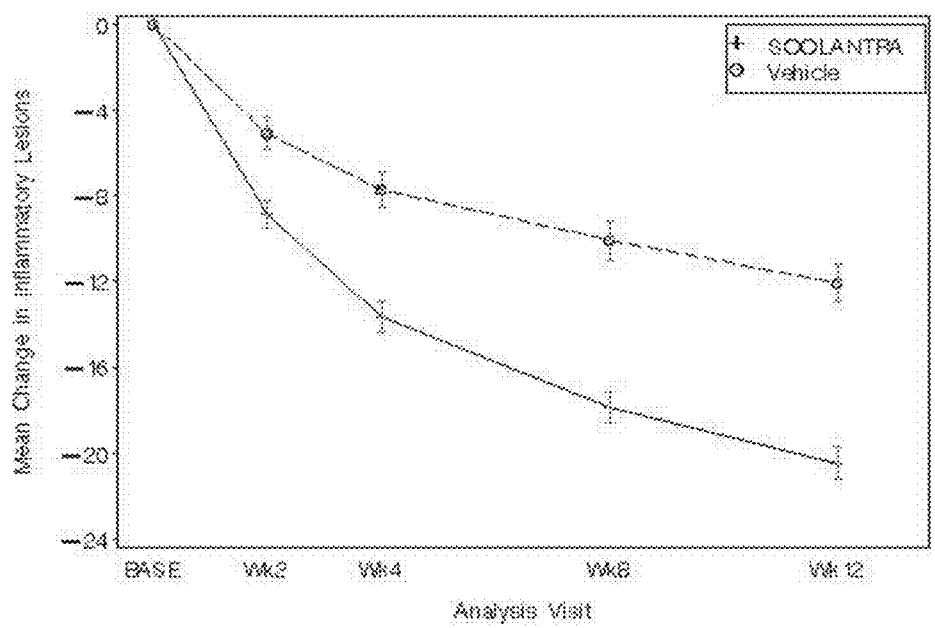
FIG. 5 shows the change from baseline in inflammatory lesion counts (ITT-LOCF): (A) mean absolute change (±standard error) in study 1; (B) mean absolute change (±standard error) in study 2; (C) median percent change in study 1; and (D) median percent change in study 2, wherein SOOLANTRA is a 1% ivermectin cream.
Figure 5B:
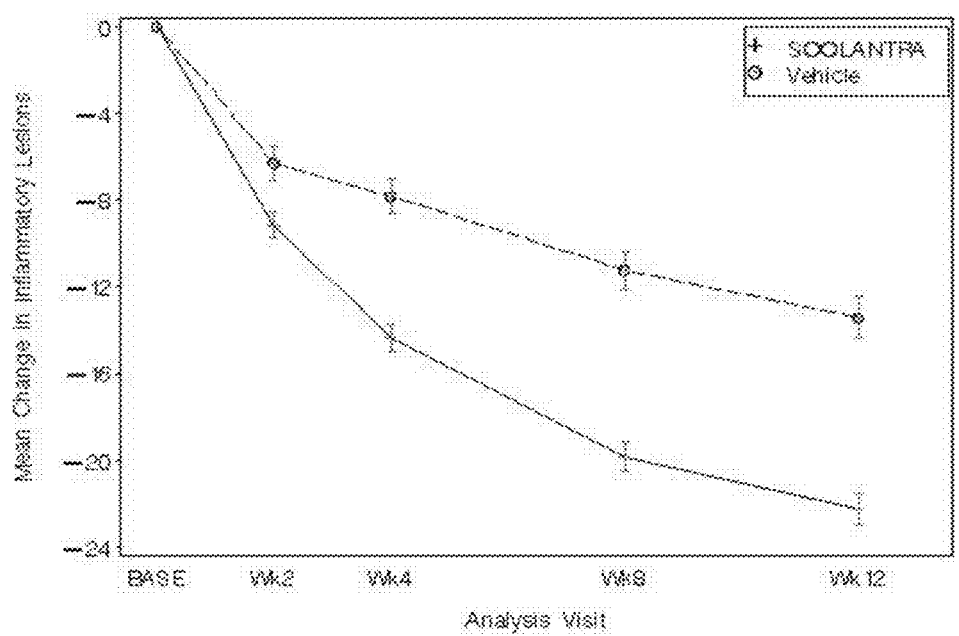
Figure 5C:
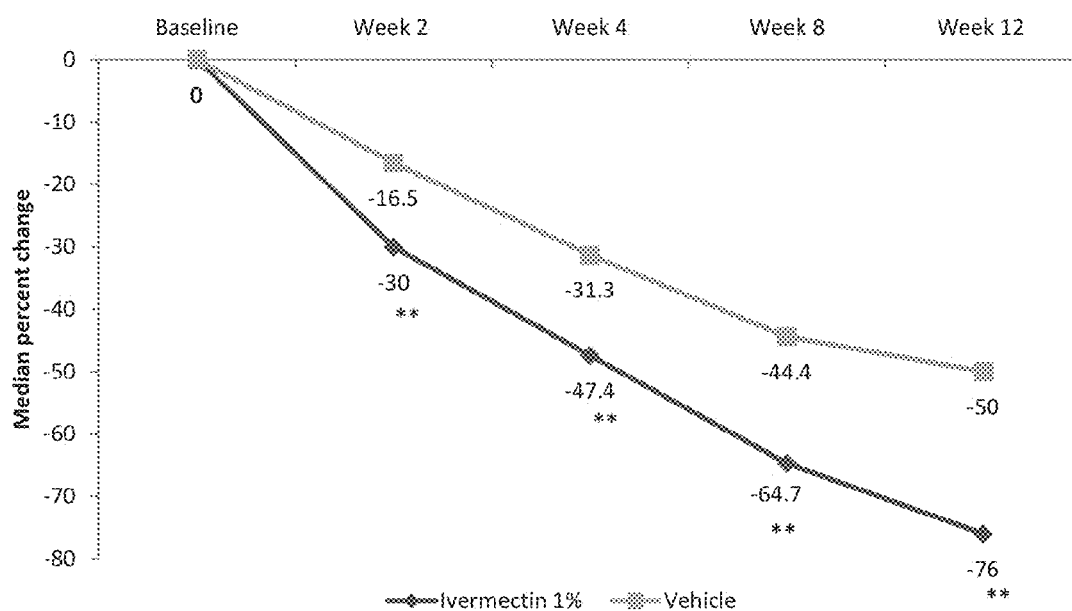
Figure 5D:
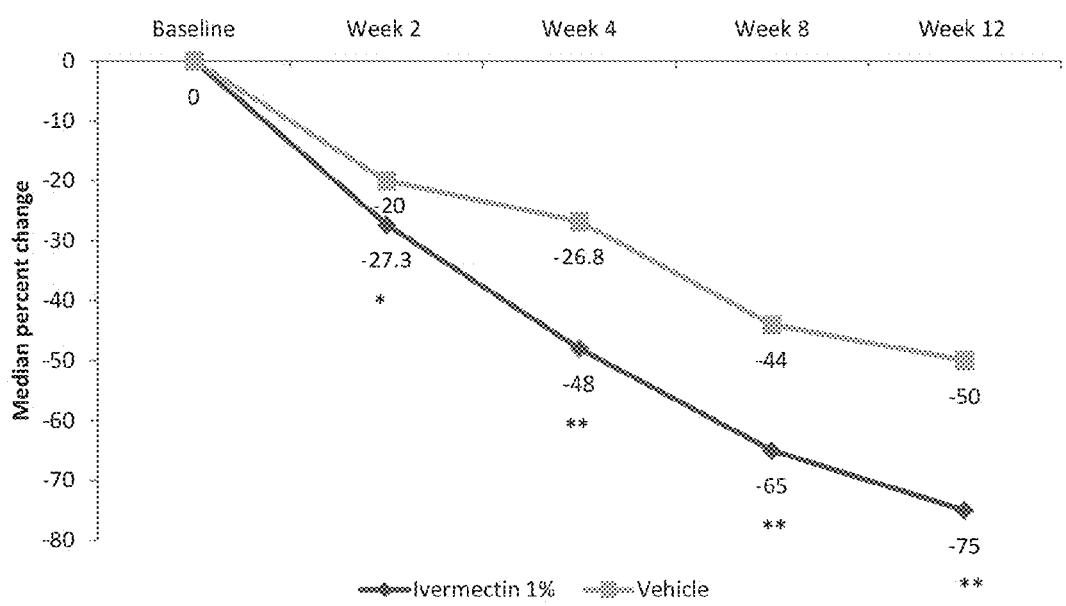

For inflammatory, lesion counts, the mean difference between IVM 1% and vehicle from baseline to week 12 was −8.13 lesions for Study 1 and −8.22 for Study 2 (both p<0.001 versus vehicle), with a 95% CI of [−10.12, −6.13] and [−10.18, −6.25], respectively (FIGS. 5A and 5B). A mean reduction of 9 lesion counts was observed at week 2 in both studies when treated with IVM 1% (FIGS. 5A and 5B). Median reduction from baseline in inflammatory lesion counts for both studies was 76.0% and 75.0%, respectively, versus 50.0% for both vehicle groups at week 12 (p<0.001), with significant difference observed by week 2 at a median reduction of 30% and 27.3% (FIGS. 5C and 5D). This significant reduction in inflammatory lesion counts as early as week 2 was exceptional when compared with similar data from treatment with metronidazole or azelaic acid.

|  | IVM 1% (N = 451) | Vehicle (N = 232) | IVM 1% (N = 459) | Vehicle (N = 229) |
|---|---|---|---|---|
| IGA |  |  |  |  |
| Number (%) of Subjects Clear or Almost Clear in the IGA at Week 12 Inflammatory Lesions | 173 (38.4) | 27 (11.6) | 184 (40.1) | 43 (18.8) |
| Mean inflammatory lesion count at baseline | 31.0 | 30.5 | 33.3 | 32.2 |
| Mean inflammatory lesion count at Week 12 | 10.6 | 18.5 | 11.0 | 18.8 |
| Mean Absolute Change (%) in Inflammatory Lesion Count from Baseline at Week 12 | −20.5 (−64.9) | −12.0 (−41.6) | −22.2 (−65.7) | −13.4 (−43.4) |

The incidence of AEs was comparable between Studies 1 and 2 (40.5% and 36.5% for IVM 1% versus 39.4% and 36.5% for vehicle, respectively). Fewer subjects in IVM 1% groups tended to report related AEs than in vehicle groups (4.2% and 2.6% versus 7.8% and 6.5%, respectively), as well as for related dermatologic AEs (3.5% and 1.5% versus 6.9% and 5.7%) and related AEs leading to discontinuation (1.3% and 0.2%, versus 1.7% for both vehicle groups). A similarly low proportion of subjects reported serious AEs for IVM 1% and vehicle groups (0.7% and 1.5% versus 0.4% and 1.7%). There were no related serious AEs. The most common related AE in Study 1 was sensation of skin burning: 8 (1.8%) in IVM 1% subjects versus 6 (2.6%) for vehicle. For Study 2, the most common related AEs for IVM 1% were pruritis and dry skin (3 subjects each (0.7%)) compared to 0 and 2 subjects (0.9%) for vehicle, respectively. In addition, laboratory tests did not demonstrate clinically significant abnormalities.

At baseline before treatment application, a large proportion of subjects presented with local cutaneous symptoms consistent with rosacea, especially mild or moderate dry skin (for Studies 1 and 2, 63.0% and 57.0% for IVM 1%, and 59.3% and 60.0% for vehicle, respectively) and mild or moderate itching (57.3% and 49.4% for IVM 1%, and 45.4% and 49.1% for vehicle). At week 12 (last available data observed), the majority of subjects had none of the 2 cutaneous symptoms. A trend was observed in terms of absence of dryness in 83-86% of IVM 1% subjects versus 72-76% for vehicle, as well as for absence of itching in 82-85% for IVM 1% versus 70-78% for vehicle.

Figure 6A:
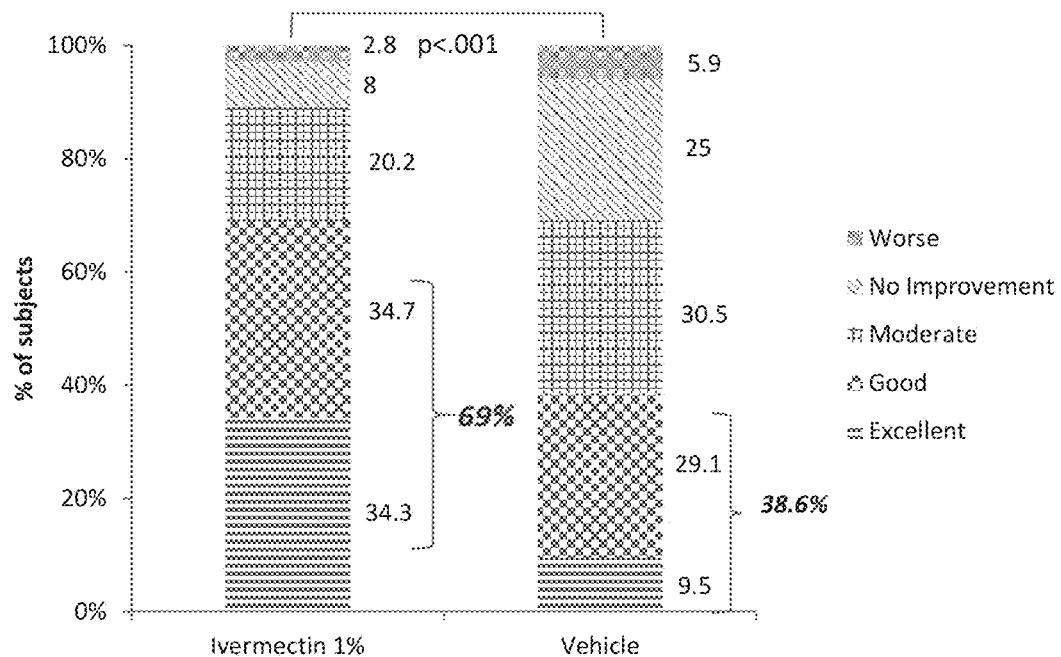
FIG. 6 show subjects' rating of rosacea improvement in (A) Study 1 and (B) Study 2 at week 12.
Figure 6B:
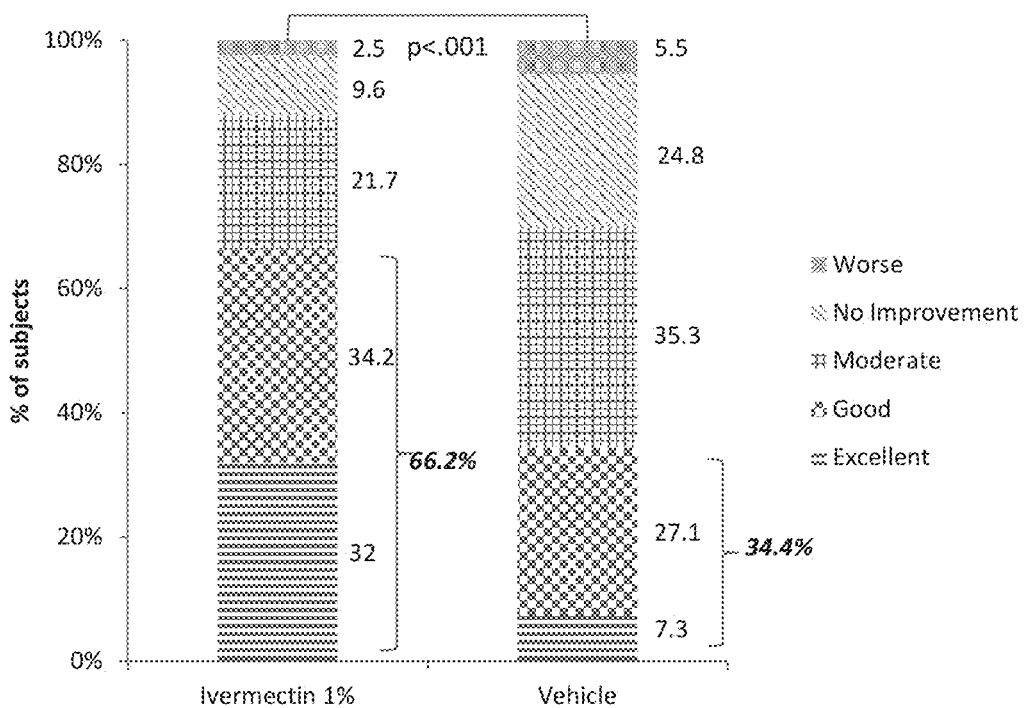
Figure 7:
FIG. 7 are photographs of a patient at Baseline and Week 12 (standard light)
Figure 7:

Improvement after treatment was rated by subjects as "excellent" or "good" by 69% and 66.2% for IVM 1% compared to 38.6% and 34.4% for vehicle (p<0.001), respectively (FIG. 6). "Excellent" improvement was reported by 34.3% and 32.0% for IVM 1% versus 9.5% and 7.3% for vehicle.

After 12 weeks of treatment, improved QoL scores were observed for subjects in the IVM 1% compared to vehicle groups. For the DLQI, it is of note that no difference between treatment groups was observed at baseline. At the end of each study, more subjects in the IVM 1% group (about 53%) than vehicle (about 35%) considered that their disease had no effect on their overall QoL (p<0.001). For RosaQoL™, improvement in QoL from baseline was higher in both studies for IVM 1% (−0.64±0.7 and −0.60±0.6 versus −0.35±0.5 for both vehicle groups (p<0.001 and p=0.001 for Studies 1 and 2, respectively). This result indicates that a higher proportion of subjects felt that their quality of life was not negatively impacted by rosacea in the group treated with IVM, compared to the control group treated with vehicle.

IGA was assessed during the second part of the studies (40 weeks). The percentages of subjects treated with IVM 1% achieving an IGA score of 0 or 1 continued to increase up to week 52, the end of the second part of the studies. The success rate (IGA=0 or 1) at week 52 was 71.1% and 76% in studies 1 and 2 respectively. In both studies, the incidences were comparable in the 2 groups of subjects treated by IVM 1% cream QD and azelaic acid 15% gel 131D across the categories of related AEs, dermatologic AEs, serious AEs, related AEs leading to discontinuation and AEs of special interests. There was no serious related AEs.

In the follow up third part of the studies, subjects treated with IVM 1% cream QD and azelaic acid 15% gel BID during the second part of the studies were comparable in reporting AEs. No subjects reported related serious AEs, related AEs leading to discontinuation.

The most frequent (>0.5% in any arm) AEs were skin disorders, and were less frequent with IVM 1% cream QD than azelaic acid 15% gel BID in both studies.

These two pivotal studies demonstrated the efficacy and safety of topical ivermectin 1% cream in the treatment of inflammatory lesions of rosacea with reproducibility. The effect was robust and highly significant (p,0.001) in all primary and secondary endpoints at week 12 (ITT-LOCF). Onset of treatment effect was observed at week 4 in each study based on both IGA and lesion counts. Onset of treatment effect was observed at week 2 in each study based on lesion counts. The ivermectin 1% cream was well tolerated and safe in both studies. No notable difference was observed between the ivermectin 1% cream QD and corresponding vehicle and azelaic acid 15% gel BID. The most frequent (>0.5% in any arm) AEs were skin disorders, and were less frequent with IVM 1% cream QD than with the respective comparator. In addition, the continued daily application of the Ivermectin 1% Cream QD up to 1 year is well tolerated, with no unexpected safety findings associated with chronic use.

In conclusion, ivermectin, such as 1% ivermectin cream, was effective and safe in treating papulopustular rosacea.

Example 4

Comparison of the Efficacy and Safety of Ivermectin 1% Cream Vs. Metronidazole 0.75% Cream This was an investigator-blinded, randomized, parallel group study comparing the efficacy and safety of ivermectin (hereafter designated IVM) 1% (w/w) cream vs. metronidazole 0.75% (w/w) cream with a 16-week period A and a 36-week period B to study recurrence. Study visits during Period A were as follows: a screening visit, and at baseline, weeks 3, 6, 9, 12 and 16.

Eligible subjects were 18 years or older, with moderate or severe papulopustular rosacea as noted by an IGA of 3 ("several small or large papules/pustules, moderate erythema") or 4 ("numerous small and/or large papules/pustules, severe erythema"), and presenting with 15-70 facial inflammatory lesions (papules and pustules).

Subjects were randomized in a 1:1 ratio to receive either IVM 1% cream (once daily, QD, at bedtime) or metronidazole 0.75% cream (twice daily, BID, as per labelling at morning and bedtime) for 16 weeks. Study drugs were applied in a thin film on the entire face (right and left cheeks, forehead, chin and nose), avoiding the upper and lower eyelids, lips, eyes and mouth. The subjects were instructed to maintain a consistent lifestyle throughout the study regarding rosacea triggers (i.e. avoiding environmental factors, certain foods, and excessive sun exposure).

Efficacy assessments at each visit were inflammatory lesion counts (papules and pustules) counted on five facial regions (forehead, chin, nose, right cheek, left cheek), and the Investigator's Global Assessment (IGA) of disease severity. Safety assessments included adverse events (AEs) throughout the study, local tolerance parameters (stinging/burning, dryness, itching) at each visit evaluated on a 4-point scale (from 0 (none) to 3 (severe)), and laboratory parameters measured at baseline, weeks 9 and 16. Other assessments included the subject's evaluation of rosacea improvement compared to their condition at baseline, and subject's appreciation questionnaire at the end of the study (regarding satisfaction with the study drug). Lastly, a quality of life questionnaire (Dermatology Life Quality Index (DLQI)) was completed at baseline and at the end of the study (week 16).

The ITT population included all subjects who were randomized and to whom the study drug was administered. The safety population included all subjects who received the study medication. The primary efficacy endpoint, percent change in inflammatory lesion counts from baseline to week 16, was analyzed using the CMH test stratified on center, with ridit transformation and row mean score difference statistic. Secondary efficacy endpoints included success rate (percent of subjects with IGA rated 0 ("clear") or 1 ("almost clear") (analyzed by CMH test stratified on center using general association statistic), IGA and absolute change in lesion counts (analyzed using ANCOVA, including treatments and analysis center as factors, and baseline as covariate). LOCF was the primary method for imputation of missing data, and multiple imputations (MI) method was used for sensitivity. Other variables were descriptively analyzed.

Figure 8:
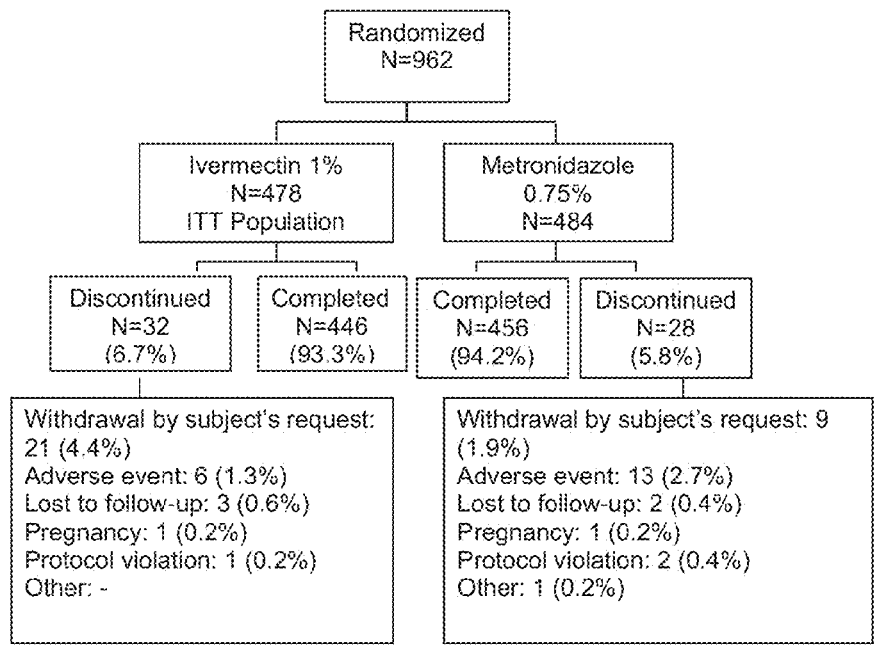
FIG. 8 shows subject disposition in a clinical study comparing the topical treatments with ivermectin and metronidazole.

A total of 1,034 subjects were screened and 962 randomized to receive IVM 1% cream (n=478) or metronidazole 0.75% cream (n=484); 902 (93.8%) completed the study (FIG. 8). Treatment groups were comparable at baseline in terms of demographics and baseline disease characteristics, with about 32 inflammatory lesions on average and the majority having moderate rosacea (83.3% with an IGA of 3) (Table 5). As expected, the quantity of product applied in the metronidazole group (BID applications) was nearly twice as much as the product applied in the IVM 1% group (QD), with a mean of 1.31 g vs. 0.72 g, respectively.

Figure 9:
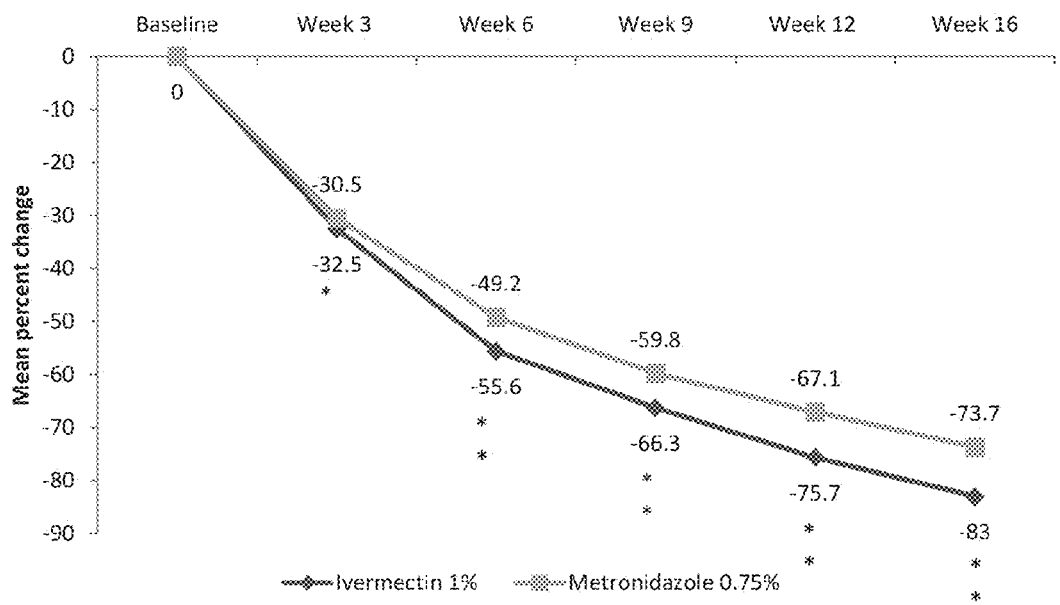
FIG. 9 illustrates the mean percent change from baseline in inflammatory lesion counts (ITT-LOCF) after the topical treatments with ivermectin and metronidazole, $*p<0.05$, $**p<0.001$.
Figure 10:
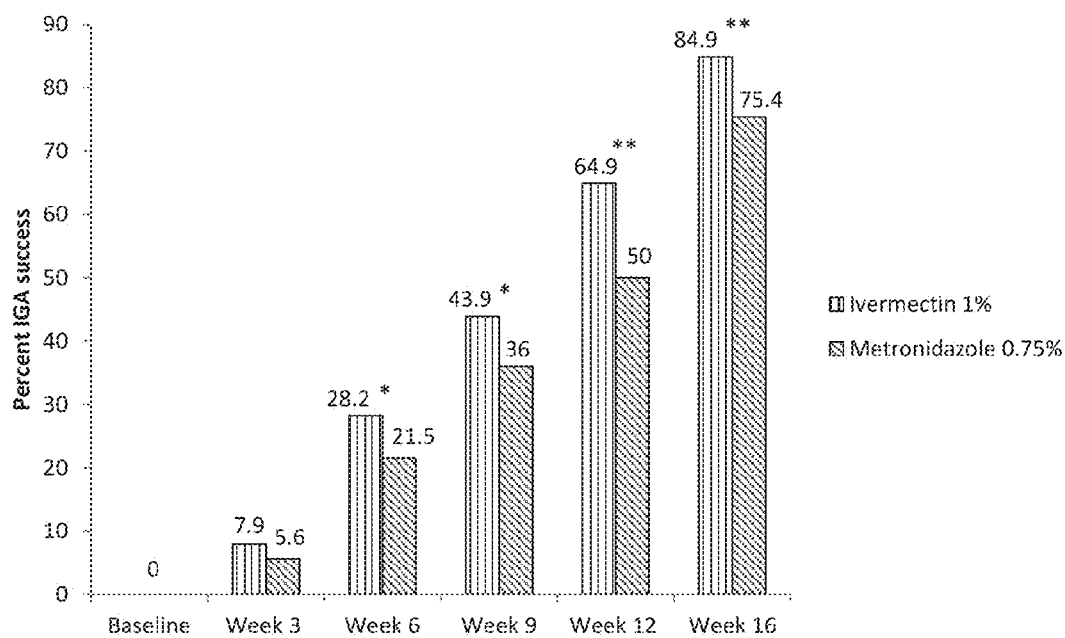
FIG. 10 shows the success rate based on IGA of "clear" or "almost clear" after the topical treatments with ivermectin and metronidazole, $*p<0.05$, $**p<0.001$.

Regarding the primary endpoint, at week 16 (ITT-LOCF), IVM 1% cream was significantly superior to metronidazole 0.75% cream in terms of percent reduction from baseline in inflammatory lesion counts (83.0% vs. 73.7%; p<0.001; FIG. 9). This difference was observed as early as week 3 (ITT-LOCF) (as soon as week 6 with ITT-MI), and this continued through week 16 (all p-values≤0.04). It should be noted that in this study, there was no study visit or assessment prior to Week 3, thus the differences in treatment could have been observed earlier than week 3 if the first study visit was conducted earlier. Similar results were found for the IGA success rate (subjects rated "clear" or "almost clear"): 84.9% for IVM 1% cream vs. 75.4% for metronidazole 0.75% cream at week 16 (ITT-LOCF) (p<0.001). As illustrated in FIG. 10, the difference in IGA was the highest at week 12 (14.9% superior for ivermectin).

About 13% more subjects were rated as "clear" in terms of IGA for IVM 1% than metronidazole 0.75% (34.9% vs. 21.7%, respectively). Furthermore, in a subgroup analysis of success rate according to IGA severity, about 20% more subjects with severe rosacea at baseline in the IVM 1% group achieved success (82.5% vs. 63.0%).

The incidence of adverse events (AEs) was similar between groups (32.4% vs. 33.1% of subjects in the IVM 1% and metronidazole 0.75% groups, respectively), as well as for related AEs (2.3% vs. 3.7%). Furthermore, a comparably low number of subjects experienced a related dermatologic AE (9 subjects (1.9%) in the IVM 1% group and 12 (2.5%) in the metronidazole 0.75% group). The most common related AE was skin irritation (3 subjects (0.6%) vs. 4 subjects (0.8%) for IVM 1% and metronidazole 0.75%, respectively). Thirteen subjects reported serious but unrelated AEs. A total of 3 subjects (0.6%) in the IVM 1% group experienced related adverse events leading to discontinuation (due to skin irritation and hypersensitivity), compared to 10 (2.1%) subjects in the metronidazole 0.75% group (due to skin irritation, allergic dermatitis, aggravation of rosacea, erythema, pruritus, and general disorders (hot feeling)).

In terms of local tolerance, the incidence of worsening from baseline was higher in the metronidazole 0.75% group for stinging/burning (15.5% vs. 11.1%), dryness (12.8% vs. 10.0%), and itching (11.4% vs. 8.8%). Laboratory tests did not demonstrate clinically significant abnormalities.

At the end of period A of this study, the majority (85.5%) of subjects in the IVM 1% group rated their global improvement as "excellent" or "good" compared to 74.8% in the metron-

TABLE 5

Demographic and baseline clinical characteristics (ITT population)

Figure 11:
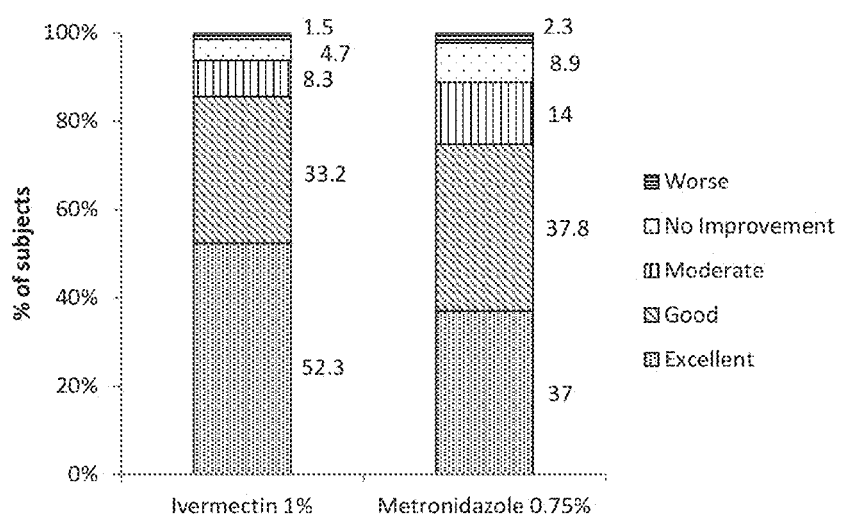
FIG. 11 shows subjects' rating of rosacea improvement after the topical treatments with ivermectin and metronidazole.

| | | Ivermectin 1% (n = 478) | Metronidazole 0.75% (n = 484) | Total (n = 962) |
|---|---|---|---|---|
| Age, years | Mean ± SD | 51.22 ± 13.40 | 51.87 ± 13.24 | 51.54 ± 13.32 |
| | Min, Max | 18, 85 | 18, 90 | 18, 90 |
| Gender, n (%) | Female | 311 (65.1%) | 316 (65.3%) | 627 (65.2%) |
| | Male | 167 (34.9%) | 168 (34.7%) | 335 (34.8%) |
| Race | Asian | 3 (0.6%) | — | 3 (0.3%) |
| | White | 475 (99.4%) | 484 (100.0%) | 959 (99.7%) |
| Skin Phototype | I | 18 (3.8%) | 17 (3.5%) | 35 (3.6%) |
| | II | 245 (51.3%) | 234 (48.3%) | 479 (49.8%) |
| | III | 178 (37.2%) | 213 (44.0%) | 391 (40.6%) |
| | IV | 36 (7.5%) | 19 (3.9%) | 55 (5.7%) |
| | V | 1 (0.2%) | 1 (0.2%) | 2 (0.2%) |
| Inflammatory lesion Counts | Mean ± SD | 32.87 ± 13.95 | 32.07 ± 12.75 | 32.46 ± 13.36 |
| Investigator Global Assessment | 3 = Moderate | 398 (83.3%) | 403 (83.3%) | 801 (83.3%) |
| | 4 = Severe | 80 (16.7%) | 81 (16.7%) | 161 (16.7%) | idazole 0.75% group. Furthermore, more subjects receiving IVM 1% reported an "excellent" improvement of their rosacea (52.3% vs. 37.0%, respectively; FIG. 11). Regarding the subject's appreciation questionnaire, more subjects in the IVM 1% group were satisfied with the study drug (76.0% vs. 61.3% in the metronidazole 0.75% group). In addition, more subjects treated by IVM 1% tended to consider the product easy to use and that the time needed for application was satisfactory, whereas more subjects found metronidazole 0.75% to be irritating (data not shown).

At baseline, the mean DLQI scores were similar between groups (6.95 for IVM 1% and 6.05 for metronidazole 0.75%, respectively). Patients treated with IVM 1% showed a higher numerical decrease in their DLQI score than patients treated with metronidazole 0.75% (−5.18 vs. −3.92; p<0.01), indicating a higher improvement in quality of life. At the end of the study, 71% of patients treated with IVM 1% reported no effect at all on their quality of life (vs. 64% for metronidazole 0.75%), which means that a higher proportion of subjects felt that their quality of life was not negatively impacted by rosacea in the group treated with IVM, compared to the group treated with metronidazole. The study drugs diverged in favor of IVM 1% in the symptoms and feelings sub-scale (level of itching, soreness, pain or stinging: "not at all" for 78.7% vs. 63.0% in the metronidazole 0.75% group; level of embarrassment or self-consciousness: "not at all" for 70.3% vs. 60.1%, respectively).

Topical metronidazole 0.75% (w/w) has been one of the most frequently used therapies in the treatment of papulopustular rosacea. In this study, IVM 1% cream was significantly superior to metronidazole 0.75% cream in terms of percent reduction from baseline in inflammatory lesion counts, with an onset of efficacy (first difference vs. metronidazole 0.75%) as early as 3 weeks (or even earlier) that continued through 16 weeks. The findings show that ivermectin is more efficacious than metronidazole, with a tendency even in patients with higher lesion counts.

An overall good safety profile was observed for IVM, and it was well-tolerated in comparison with metronidazole. It is not surprising that for both products, patients experienced a similarly low number of related adverse events, particularly since the tolerability of metronidazole is known to be satisfactory. Metronidazole's higher incidence of worsening from baseline concerning stinging/burning, dryness, and itching may be attributed to the usual signs and symptoms of rosacea. Nevertheless, this affected the level of quality of life as measured by the DLQI, as more patients in the metronidazole group reported itching, soreness, pain or stinging.

Patient-reported outcomes for IVM 1% cream were consistent with its superior efficacy results. More patients using IVM indicated that the product was easy to use and that the time needed for application was satisfactory, implying that the daily application is more convenient than metronidazole's twice-daily regimen. Related to quality of life measures, fewer patients using IVM considered themselves to be embarrassed or self-conscious. Thus, ivermectin appears to be adapted to the complex etiology of rosacea, and in the study IVM 1% cream demonstrated superiority to metronidazole 0.75% cream in terms of inflammatory lesion reduction. As noted in the afore-mentioned Cochrane review, few robust studies have compared topical metronidazole with another rosacea treatment and in three identified studies, topical metronidazole was either non-significantly different or less effective than azelaic acid.[8] While metronidazole has been used in the past as a reasonable treatment for the papulo-pustular lesions of rosacea, its efficacy is surpassed by that of ivermectin along with the advantage of once-daily dosing.

The relapse among subjects successfully treated at the end of the Period A was studied during the treatment free Period B (36 weeks). At the end of Period A, only subjects with an IGA of "0" or "1" (clear or almost clear) were eligible for entering Period B. Then, their study treatment was discontinued and the subjects were followed for up to 8 months (36 weeks). In case of reoccurrence of an IGA of at least "2" (mild) at any time during Period B, the subjects were retreated with the same treatment received during the Period A. The re-treatment was stopped as soon as the IGA was back to "0" or "1" (clear or almost clear). The maximum duration of re-treatment was 16 consecutive weeks to mimic the Period A treatment duration. In order to characterize the relapses, the following parameters were assessed: (1) time of first relapse (time elapsed between Week 16 and first reoccurrence of IGA at "2", "3" or "4" inducing a retreatment course), (2) relapse rate (percentage of subjects with reoccurrence of IGA at "2", "3" or "4" after a period free of study treatment) and (3) number of days free of treatment.

At the start of Period B, treatment groups were comparable with respect to the demographic. Of the total 757 subjects included in Period B (399 in Ivermectin 1% and 358 in Metronidazole 0.75% groups, respectively), 504 (66.6%) were female, 754 (99.6%) were Caucasian and the mean age was 51.9 years. In terms of disease characteristics, the means inflammatory lesion counts were similar in both groups (median 2.0). But, the proportion of subjects with an IGA of 0 was higher in Ivermectin group than in Metronidazole group (41.6% versus 29.1%) due to the higher efficacy of Ivermectin treatment from Period A.

TABLE 6

End of Period A disease characteristics of subjects entering Period B

|  |  | Ivermectin | Metronidazole | TOTAL |
|---|---|---|---|---|
| Inflammatory lesion counts | N | 399 | 358 | 757 |
|  | Mean | 2.58 | 2.96 | 2.76 |
|  | SD | 3.20 | 3.42 | 3.31 |
|  | Median | 2.00 | 2.00 | 2.00 |
|  | Min~Max | 0~19 | 0~24 | 0~24 |
|  | P25~P75 | 0~4 | 0~4 | 0~4 |
| Investigator Global Assessment | N | 399 | 358 | 757 |
|  | 0 = Clear | 166 (41.6%) | 104 (29.1%) | 270 (35.7%) |
|  | 1 = Almost Clear | 233 (58.4%) | 254 (70.9%) | 487 (64.3%) |
| Nodules | N | 399 | 358 | 757 |
|  | 0 | 397 (99.5%) | 357 (99.7%) | 754 (99.6%) |
|  | 1 | 2 (0.5%) | 1 (0.3%) | 3 (0.4%) |
| Papules | N | 399 | 358 | 757 |
|  | Mean | 2.27 | 2.56 | 2.40 |
|  | SD | 2.77 | 2.83 | 2.80 |
|  | Median | 2.00 | 2.00 | 2.00 |
|  | Min~Max | 0~16 | 0~17 | 0~17 |
|  | P25~P75 | 0~4 | 0~4 | 0~4 |
| Pustules | N | 399 | 358 | 757 |
|  | Mean | 0.32 | 0.40 | 0.36 |
|  | SD | 0.91 | 1.20 | 1.06 |
|  | Median | 0.00 | 0.00 | 0.00 |
|  | Min~Max | 0~9 | 0~12 | 0~12 |
|  | P25~P75 | 0~0 | 0~0 | 0~0 |

The time to first relapse, defined as time elapsed between Week 16 and first reoccurrence of IGA at "2", "3" or "4" was analyzed following 2 definitions: (1) the first one was based on IGA only; and (2) the second one took also into account any major deviations by imputing relapse the day of first major deviation. For each definition, a sensitivity analysis was performed by imputing relapse 4 weeks after discontinuation for all subjects who discontinued early from Period B without relapse. Relapse rates followed the same convention analyses as the time to relapse.

Figure 12:
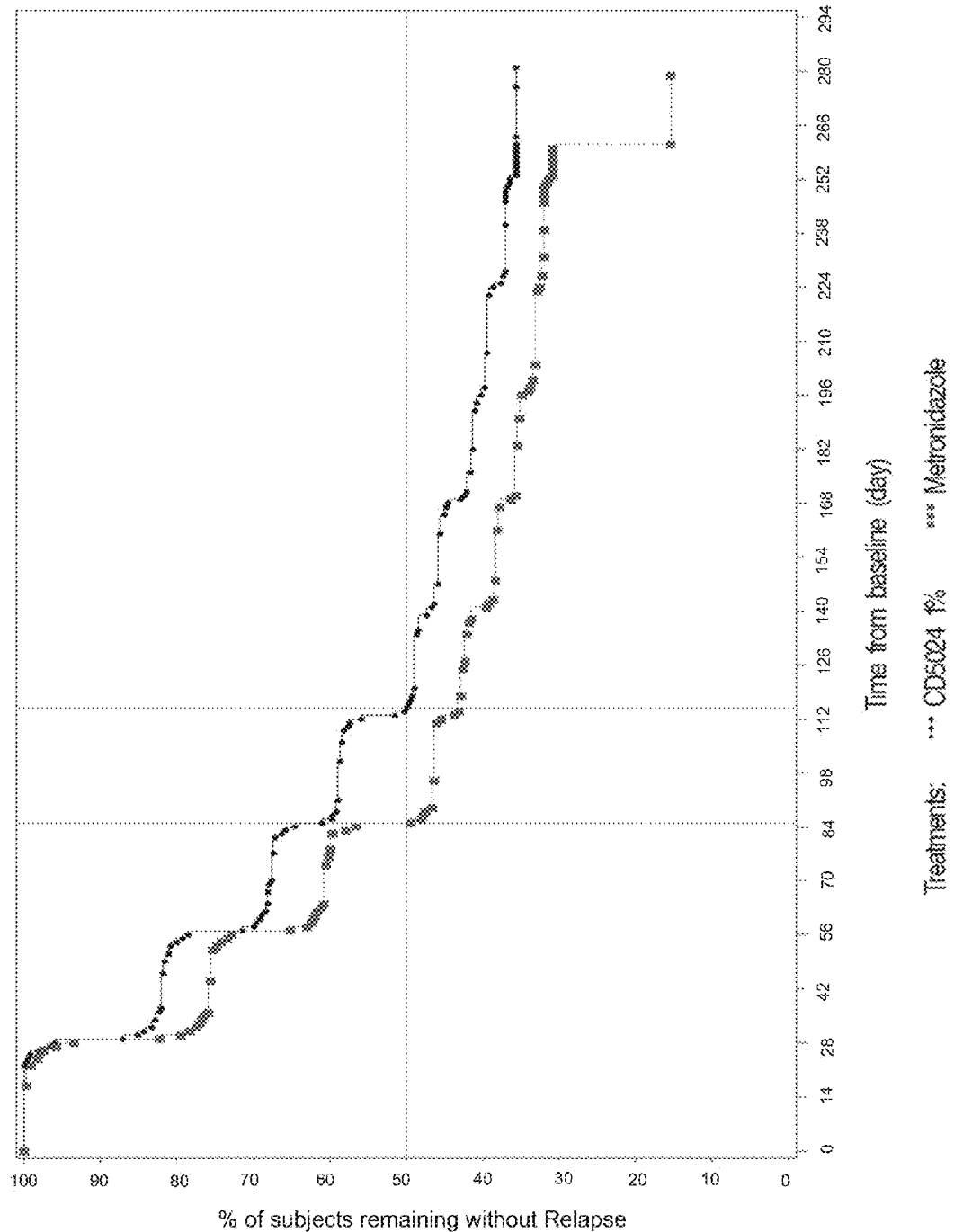
FIG. 12. shows time to first relapse defined as first re-occurrence of IGA≥2 after the successful treatments with ivermectin and metronidazole.

The median times to first relapse were 115 days for ivermectin 1% QD and 85 days for Metronidazole 0.75% BID (p=0.0365), the relapse rates were 62.7% and 68.4% respectively (Table 7). See also FIG. 12. When conducting the sensitivity analysis by imputing relapse 4 weeks later to subjects who discontinued early without relapse, the medians were 114 days and 85 days (p=0.0594) and the relapse rates were 66.2% and 70.4%, respectively. Similar results were obtained when taking also into account the day of first major deviation.

TABLE 7

|  | IVM 1% | Metronidazole | p-value (1) |
|---|---|---|---|
| N | 399 | 358 | 0.0365 |
| Median and 95% Confidence Interval | 115.0 [113; 165] | 85.0 [85; 113] | — |
| Mean ± Standard Error | 147.0 ± 4.66 | 133.6 ± 5.13 | — |

Relapse is based on IGA only
(1) Logrank test

Number of days free of treatment was defined for each subject enrolled in period B as the time interval between a visit where IGA is assessed as 0 or 1 and the next visit. The number of treatment-free days is the summation over all visits of period B meeting this criterion. An additional analysis was also performed by subtracting from the days free of treatment any time interval between visits when the subject while being IGA 0 or 1 had a major protocol deviation.

Based on IGA score showed a mean days free of treatment of 183 days for ivermectin 1% QD versus 170 clays for metronidazole (p=0.026). When taking into account the protocol deviations the mean days free of treatment remained nearly the same 181 days versus 168 days (p=0.021) in favor of ivermectin 1% QD.

Ivermectin 1% cream QD treatment resulted in a statistically significant extended remission (i.e. delayed time to first relapse, and increase in the number of treatment free clays) of rosacea when compared to Metronidazole 0.75% BID in subjects who were successfully treated (IGA 0 (clear) or 1 (almost clear)) for 16 weeks. There was also a numerical trend in favor of Ivermectin 1% cream QD for the relapse rates (62.7% and 68.4% in the Ivermectin 1% group and Metronidazole 0.75% group, respectively). It should be noted that the differences observed in favor of Ivermectin 1% in Period B are presumably the consequence of the higher efficacy of Ivermectin compared to Metronidazole observed at the end of Period A, with a higher proportion of subjects with an IGA=0 in the Ivermectin group (41.6% and 29.1% in Ivermectin and Metronidazole, respectively).

The overall pharmacoeconomic benefit of Ivermectin 1% cream QD versus Metronidazole 0.75% cream BID over the one year duration of the study (Period A & B), is considerable when viewed as the sum of the following elements: benefit of Ivermectin over Metronidazole observed at the end of Period A (84.9% of success in Ivermectin group Vs. 75.4% in Metronidazole group), time to first relapse (115 Vs. 85 days), relapse rate (62.7% Vs. 68.4%) and number of days free of treatment (183.4 Vs. 170.4).

Example 5

Plasma Pharmacokinetic Study

A multi-center, open-label, single treatment study was conducted to assess the pharmacokinetic (PK) profile of ivermectin 1% (w/w) cream in subjects with severe PPR. A maximized dose of about 2 mg/cm$^2$ (1 g of ivermectin 1% (w/w) cream, equivalent to 10 mg ivermectin per application) was applied to the face once daily for 4 weeks. The treatment was followed by a 28-Day follow-up period.

A total of seventeen subjects received at least one dose of treatment. All subjects provided PK parameters at some time points, but fifteen (9 females and 6 males) provided full PK profiles at Days 0, 14 and 28. These fifteen subjects had an inflammatory lesion count of 27 to 88 lesions and severe papulo-pustular rosacea (IGA score 4) at baseline (pretreatment).

Blood samples for determination of ivermectin levels in plasma were taken from all subjects before application on Days 0, 7, 14, 21 and 28 (pre-dose samples corresponding to $C_{min}$). Additional blood samples were taken on Days 0, 14 and 28 at 1, 3, 6, 9 and 12 hours after application. At, the end of the 28-Day treatment, blood samples were taken on Days 29, 30, 32, 35, 38, 42, 49 and 56 during the follow-up period. The plasma was isolated and frozen (−20° C.) pending analysis.

The pharmacokinetic analysis was performed. From the individual plasma concentrations, the pharmacokinetic parameters were determined by non-compartmental method Kinetica™ sofware, version 4.3, InnaPhase Corporation, Philadelphia, USA).

During the treatment period, the following parameters were measured:
(1) $C_{min}$: The pre dose plasma concentration of the drug at Days 0 (24 hours after D0, pre-dose of Day 1), 7, 14, 21 and 28;
(2) $C_{max}$: The observed peak drug concentration at Days 0, 14 and 28;
(3) $T_{max}$ The time at which $C_{max}$ occurs at Days 0, 14 and 28;
(4) $AUC_{0-24\,H}$ Area under the concentration-time curve from pre-application (T0) through 24 hours post dosing corresponding to the dosing interval. $AUC_{0-24\,H}$ was calculated by the mixed linear-logarithmic trapezoidal method at Day 0, 14 and 28. BLQ was imputed as zero in the individual PK profile.

During the follow up period, the following parameters were measured:
(1) AUC0-t: Area under the concentration-time curve calculated by the mixed linear-logarithmic trapezoidal method from T0 up to the sampling time corresponding to the last quantifiable concentration (Clast);
(2) Kel: The elimination rate constant value (kel) was obtained by linear regression of log-linear terminal phase of concentration-time profile using at least 3 data points, excluding Cmax, otherwise kel was not determined. The acceptability criteria for determination of kel was a coefficient of regression more or equal to 0.98. When kel was not determined, AUC0-inf and t½ were not reported;
(3) t½: The terminal half-life value (t½) was calculated using the equation ln2/kel;
(4) AUC0-inf: Area under the plasma concentration-time curve calculated by the mixed linear-logarithmic trapezoidal method from T0 and extrapolated to time infinity as: AUC0-inf=AUC0-t+Clast/kel.

When the extrapolation represented more than 20%, $AUC_{0-inf}$ and $t_{1/2}$ were reported. Mean values, standard deviation (SD), lowest individual value (Min), maximal individual value (Max) and coefficient of variation (CV) were calculated and reported on each variables (Arithmetic mean for AUC, $C_{max}$, $T_{max}$ and harmonic mean for $t_{1/2}$). Conversely to the protocol, the standard error of mean (SEM) were not calculated and not reported. In addition a statistical analysis was performed on ivermectin specific parameters (including the accumulation ratios).

A total of seventeen subjects received at least one dose of treatment. All subjects provided PK parameters at some time points, but fifteen (9 females and 6 males) provided full PK profiles at Days 0, 14 and 28. The PK parameters from all the subjects are presented in this report (17 subjects at Days 0/1 and 15 subjects in the subsequent days).

No unacceptable deviations were observed between the actual and theoretical sampling times (according to pre-defined acceptable range). Consequently, the theoretical sampling times were used for PK analysis. Individual ivermectin plasma concentrations determined during the treatment period are summarized in Table 8.

After the very latest topical application of ivermectin (Day 28), the apparent terminal half-life determined from 14 enrolled subjects was 145 hours (range 92-238 hours), the last quantifiable concentration being observed approximately 24 days after application. In addition the total systemic exposure at Day28 ($AUC_{0\text{-}inf}$) was 312±173 ng·h/mL. This prolonged apparent half-life indicates that ivermectin was slowly cleared from plasma after the ivermectin treatment was stopped.

After a 28-Day once daily topical application of ivermectin cream 1%, the systemic exposure of ivermectin over the dosing interval calculated at Day 14 ($AUC_{0\text{-}24\ H}$: 36.14±15.56 ng·h/mL, range 13.69-75.16 ng·h/mL) and at Day 28 ($AUC_{0\text{-}24\ H}$: 35.43±14.42 ng·h/mL, range: 12.89-70.08 ng·h/mL) were similar, indicating that the steady state was reached

TABLE 8 pharmacokinetics parameters at various treatment period: Mean ± SD (N = 15)

| Parameters | Day0[a] | Day7[b] | Day 14 | Day 21 | Day 28 |
|---|---|---|---|---|---|
| Pre-dose/$C_{min}$ (ng/mL): | | | | | |
| mean ± SD | 0.37 ± 0.21[a] | 1.17 ± 0.88 | 1.26 ± 0.53[c] | 1.36 ± 0.66[c] | 1.36 ± 0.63 |
| Min-Max | [0.17-0.86] | [0.56-3.26] | [0.58-2.34] | [0.66-3.25] | [0.53-3.00] |
| $C_{max}$ (ng/mL): | | | | | |
| mean ± SD | 0.69 ± 0.49 | | 2.10 ± 1.04 | | 1.74 ± 0.77 |
| Min-Max | [0.19-1.76] | | [0.69-4.02] | | [0.58-3.36] |
| $T_{max}$ (h): | | | | | |
| mean ± SD | 9 ± 6 | | 10 ± 8 | | 11 ± 4 |
| Min-Max | [1-24] | | [0-24] | | [3-24] |
| $AUC_{0\text{-}24\ H}$ (ng·h/mL): | | | | | |
| mean ± SD | 9.29 ± 5.40 | | 36.14 ± 15.56 | | 35.43 ± 14.42 |
| Min-Max | [3.16-21.28] | | [13.69-75.16] | | [12.89-70.08] |

[a] N = 17,
[b] N = 13,
[c] N = 1

Figure 13:
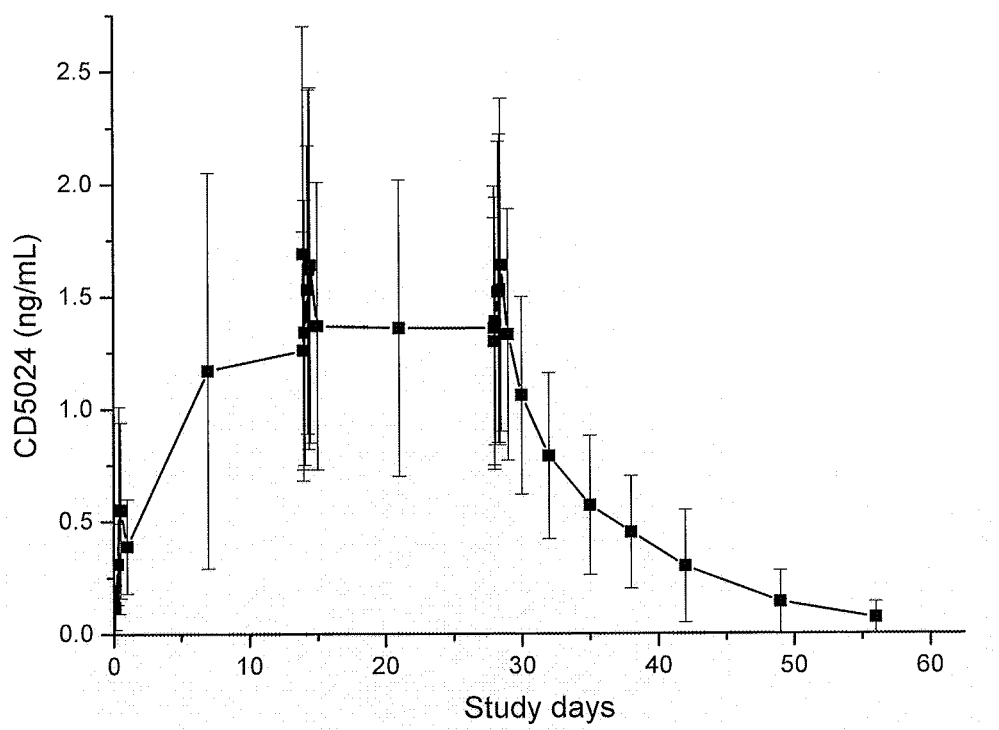
FIG. 13. illustrates overall mean ivermectin plasma concentrations (±SD, with N=15).

The arithmetic mean ivermectin plasma profiles over the 28-Day treatment application are exhibited in FIG. 13. The mean±SD and the range (Min-Max) values of $C_{min}$, $C_{max}$, and $AUC_{0\text{-}24\ H}$ on all sampling days are given up in Table 8.

After one single topical application of ivermectin cream 1%, quantifiable ivermectin levels were found in the plasma of the 17 subjects assigned to treatment. A high inter-individual variability was observed as evidenced by the coefficient of variation (CV) ranging from 57 to 71%. After a single topical application (Day 0) a flat PK profile was observed over the dosing interval, plasma concentrations of ivermectin peaked within 9 hours post dose (0.69 ng/mL range: 0.19-1.76 ng/mL) and then slowly decreased thereafter up to 0.37 ng/mL, 24 hours post dose.

After a 28-day of once daily topical application of ivermectin cream 1%, the systemic exposures are higher than the ones calculated after one single application. A lower inter-individual variability was observed after repeated dosing, with CV ranging from 39% to 46%.

The systemic exposures over the dosing interval calculated at Day 14 ($AUC_{0\text{-}24\ H}$: 36.14±15.56 ng·h/mL) and at Day 28 ($AUC_{0\text{-}24\ H}$: 35.43±14.42 ng·h/mL) were similar, indicating that the steady state was reached as early as 14 days after the initial administration. The same tendency was observed with the pre-dose plasma concentrations. The mean (±SD) pre-dose concentrations of ivermectin were 1.26±0.53 ng/mL, 1.36±0.66 ng/mL and 1.36±0.63 ng/mL at Day 14, Day 21 and Day 28, respectively.

by Day 14. At steady state (after 2 weeks of treatment), the highest mean (±standard deviation) plasma concentrations of ivermectin peaked within 10±8 hours post-dose dose (Cmax: 2.10±1.04 ng/mL range: 0.69-4.02 ng/mL) and the highest mean (±standard deviation) AUC 0-24 hr was 36.14±15.56 ng·hr/mL (range: 13.69-75.16 ng·hr/mL). These levels obtained under steady-state conditions are lower than those observed following oral administration of ivermectin (relative bioavailability of 16%). Additional systemic exposure assessment in a longer treatment duration (Phase 3 study) evidenced that there was no plasma accumulation of ivermectin over a 52-week treatment period, indicating that ivermectin is safe and can be administered for a long period of time.

At the end of the 28-Day application period, ivermectin was slowly cleared from the plasma with an apparent plasma terminal half-life of 145 hours, the last quantifiable concentration being observed approximately 24 days after application. This terminal half-life is more prolonged than the one published for an oral administration of ivermectin. The $t_{1/2}$ for ivermectin orally administered is typically around 18 hours, ranging from about 12 to 20 hours (Fink et at Guzzo et al). This prolonged terminal half-life after topical administration suggest that the rate limiting step in plasma ivermectin concentration decrease is the ivermectin disappearance from the administration site rather than the elimination rate. The term of flip-flop is used to describe this phenomenon (Toutain et al, 2004, supra).

In conclusion, the once daily topical treatment with 1% ivermectin is safe and can be conducted for as long as it is needed without causing any safety concerns.

REFERENCES

1. Gupta A K, Chaudhry M M. Rosacea and its management: an overview. *J Eur Acad Dermatol Venereol* 2005; 19(3): 273-85.
2. National Rosacea Society. Rosacea Now Estimated to Affect at Least 16 Million Americans. Rosacea Review, winter 2010 issue. Retrieved Dec. 10, 2013 from http://www.rosacea.org/rr/2010/winter/article_1.php
3. Wilkin J, Dahl M, Detmar M, et al. Standard classification of rosacea: Report of the National Rosacea Society Expert Committee on the classification and staging of rosacea. *J Am Acad Dermatol* 2002; 46: 584-587.
4. Balkrishnan R, McMichael A J, Hu J Y, Camacho F T, Shew K R, Bouloc A, et al. Correlates of health-related quality of life in women with severe facial blemishes. *Int J Dermatol* 2006; 45(2):111-5.
5. Del Rosso J Q, Gallo R L, Tanghetti E, Webster G, Thiboutot D. An evaluation of potential correlations between pathophysiologic mechanisms, clinical manifestations, and management of rosacea. *Cutis* 2013; 91(3 Suppl):1-8.
6. Holmes A D. Potential role of microorganisms in the pathogenesis of rosacea. *J Am Acad Dermatol* 2013; 69(6): 1025-32.
7. Pelle M T, Crawford G H, James W D. Rosacea: II. Therapy. *J Am Acad Dermatol* 2004; 51(4):499-514.
8. van Zuuren E J, Kramer S F, Carter B R, Graber M A, Fedorowicz Z. Effective and evidence-based management strategies for rosacea: summary of a Cochrane systematic review. *Br J Dermatol* 2011; 165(4):760-81.
9. Elewski B E Results of a national rosacea patient survey: common issues that concern rosacea sufferers. *J Drugs Dermatol* 2009; 8(2):120-3.
10. Ci X, Li H, Yu Q, Zhang X, Yu L, Chen N, et al. Avermectin exerts anti-inflammatory effect by downregulating the nuclear transcription factor kappa-B and mitogen-activated protein kinase activation pathway. *Fundam Clin Pharmacol* 2009; 23(4):449-55.
11. Yanagihara K, Kadoto J, Kohno S. Diffuse panbronchiolitis-pathophysiology and treatment mechanisms. *Int J Antimicroh Agents* 2001; 18 Suppl 1:S83-7.
12. Ianaro A, Ialenti A, Maffia P, Sautebin L, Rombolà L, Carnuccio R, et al. Anti-inflammatory activity of macrolide antibiotics. *J Pharmacol Exp Ther* 2000; 292(1): 156-63.
13. Campbell W C. History of avermectin and ivermectin, with notes on the history of other macrocyclic lactone antiparasitic agents. *Curr Pharm Biotechnol* 2012; 13(6): 853-65.
14. Forstinger C, Kittler H, Binder M. Treatment of rosacea-like demodicidosis with oral ivermectin and topical permethrin cream. *J Am Acad Dermatol* 1999; 41: 775-7.
15. Trendelenburg M, Büchner S, Passweg J, Rätz Bravo A R, Gratwohl A. Disseminated scabies evolving in a patient undergoing induction chemotherapy for acute myeloblastic leukaemia. Ann Hematol 2001; 80(2):116-8.
16. Pariser D M, Meinking T L, Bell M, Ryan W G. Topical 0.5% ivermectin lotion for treatment of head lice. *N Engl J Med* 2012; 367(18):1687-93.
17. Finlay A Y, Khan G K. Dermatology Life Quality Index (DLQI)—a simple practical measure for routine clinical use. Clin Exp Dermatol 1994; 19(3): 210-6.
18. Nicholson K, Abramova L, Chren M M, Yeung J, Chon S Y, Chen S C. A pilot quality-of-life instrument for acne rosacea. J Am Acad Dermatol 2007; 57(2):213-21.
19. Zhang X, Song Y, Ci X et al. Ivermectin inhibits LPS-induced production of inflammatory cytokines and improves LPS-induced survival in mice. Inflamm Res 2008; 57:524-9.
20. Gerber P A, Buhren B A, Steinhoff M, Homey B. Rosacea: The cytokine and chemokine network. J Investig Dermatol Symp Proc 2011; 15(1):40-7.
21. Wolstenholme A J, Rogers A T. Glutamate-gated chloride channels and the mode of action of the avermectin/milbemycin anthelmintics. Parasitology 2005; 131 Suppl:S85-95.
22. Damian D. *Demodex* infestation in a child with leukemia: treatment with ivermectin and permethrin. Int J Dermatol 2003; 42:724-6.
23. Filho P A, Hazarbassanov R M, Grisolia A B et al. The efficacy of oral ivermectin for the treatment of chronic blepharitis in patients tested positive for *Demodex* spp. Br J Ophthalmol 2011; 95: 893-5.
24. Powell F C. Rosacea and the pilosebaceous follicle. Cutis 2004; 74 (3 Suppl): 9-12.
25. Marks R. The enigma of rosacea. J Dermatol Treat 2007; 18:326-8.
26. Forton F M N. Papulopustular rosacea, skin immunity and *Demodex: pityriasis folliculorum* as a missing link. 0.1 Eur Acad Dermatol Venereol 2012; 26:19-28.
27. Reinholz M, Ruzicka T, Schauber J. Cathelicidin L L-37: An antimicrobial peptide with a role in inflammatory skin disease. Ann Dermatol 2012; 24(2):126-135.
28. Millikan L. Rosacea as an inflammatory disorder: a unifying theory? Cutis 2004; 73(suppl 1): 5-8.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of treating inflammatory lesions of rosacea in a subject in need thereof, comprising topically administering, once daily, to a skin area affected by the inflammatory lesions of rosacea a pharmaceutical composition comprising 1% by weight ivermectin and a pharmaceutically acceptable carrier, wherein as early as 2 weeks after the initial administration of the pharmaceutical composition, a significant reduction in inflammatory lesion count is observed.

2. The method of claim 1, wherein the treatment results in more reduction in inflammatory lesion count in the subject in comparison to that achieved by topically administering to the subject, twice daily, a second pharmaceutical composition comprising 0.75% by weight metronidazole.

3. The method of claim 1, wherein the treatment results in longer relapse-free time of the inflammatory lesions of rosacea in the subject in comparison to that achieved by twice daily topically administering to the subject a second pharmaceutical composition comprising 0.75% by weight metronidazole.

4. The method of claim 1, wherein the treatment has a median time to first relapse of 110 days or longer.

5. The method of claim 1, wherein the subject has moderate to severe papulopustular rosacea before the treatment.

6. The method of claim 5, wherein the subject has 15 or more of the inflammatory lesions before the treatment.

7. The method of claim 1, wherein a steady state of plasma concentration of ivermectin is reached in the subject as early as 2 weeks after the initial administration of the pharmaceutical composition to the subject, wherein the steady state has a $C_{max}$ of ivermectin of 0.5-10 ng/mL, and an $AUC_{0\text{-}24\ hr}$ of 10-100 ng·hr/mL in the subject.

8. The method of claim 1, wherein the pharmaceutical composition further comprises one or more ingredients selected from the group consisting of: an oily phase comprising dimethicone, cyclomethicone, isopropyl palmitate and/or isopropyl myristate, the oily phase further comprising fatty substances selected from the group consisting of cetyl alcohol, cetostearyl alcohol, stearyl alcohol, palmitostearic acid, stearic acid and self-emulsifiable wax; at least one surfactant-emulsifier selected from the group consisting of glyceryl/PEG100 stearate, sorbitan monostearate, sorbitan palmitate, Steareth-20, Steareth-2, Steareth-21 and Ceteareth-20; a mixture of solvents and/or propenetrating agents selected from the group consisting of propylene glycol, oleyl alcohol, phenoxyethanol and glyceryl triacetate; one or more gelling agents selected from the group consisting of carbomers, cellulose gelling agents, xanthan gums, aluminum magnesium silicates but excluding aluminum magnesium silicate/titanium dioxide/silica, guar gums, polyacrylamides and modified starches; and water.

9. The method of claim 1, wherein the topical administration of the pharmaceutical composition to the subject results in a mean terminal half-life of ivermectin of about 145 hours in the subject.

10. A method of treating inflammatory lesions of rosacea in a subject in need thereof, comprising topically administering, once daily, to a skin area affected by the inflammatory lesions a pharmaceutical composition comprising 1% by weight ivermectin and a pharmaceutically acceptable carrier, wherein as early as 2 weeks after the initial administration of the pharmaceutical composition to the subject, a significant reduction in inflammatory lesion count is observed and a steady state of plasma concentration of ivermectin is reached in the subject, and the steady state has a mean $C_{max}$ of ivermectin of 2.10±1.04 ng/mL with a range of 0.69-4.02 ng/mL, and a mean $AUC_{0\text{-}24\ hr}$ of 36.14±15.56 ng·hr/mL with a range of 13.69-75.16 ng·hr/mL.

11. The method of claim 10, wherein the treatment results in more reduction in inflammatory lesion count in the subject in comparison to that achieved by topically administering to the subject, twice daily, a second pharmaceutical composition comprising 0.75% by weight metronidazole.

12. The method of claim 10, wherein the treatment results in longer relapse-free time of the inflammatory lesions of rosacea in the subject in comparison to that achieved by twice daily topically administering to the subject a second pharmaceutical composition comprising 0.75% by weight metronidazole.

13. The method of claim 10, wherein the treatment has a median time to first relapse of 110 days or longer.

14. The method of claim 10, wherein the subject has moderate to severe papulopustular rosacea before the treatment.

15. The method of claim 14, wherein the subject has 15 or more of the inflammatory lesions before the treatment.

16. The method of claim 10, wherein the pharmaceutical composition further comprises one or more ingredients selected from the group consisting of: an oily phase comprising dimethicone, cyclomethicone, isopropyl palmitate and/or isopropyl myristate, the oily phase further comprising fatty substances selected from the group consisting of cetyl alcohol, cetostearyl alcohol, stearyl alcohol, palmitostearic acid, stearic acid and self-emulsifiable wax; at least one surfactant-emulsifier selected from the group consisting of glyceryl/PEG 100 stearate, sorbitan monostearate, sorbitan palmitate, Steareth-20, Steareth-2, Steareth-21 and Ceteareth-20; a mixture of solvents and/or propenetrating agents selected from the group consisting of propylene glycol, oleyl alcohol, phenoxyethanol and glyceryl triacetate; one or more gelling agents selected from the group consisting of carbomers, cellulose gelling agents, xanthan gums, aluminum magnesium silicates but excluding aluminum magnesium silicate/titanium dioxide/silica, guar gums, polyacrylamides and modified starches; and water.

17. The method of claim 10, wherein the pharmaceutical composition further comprises carbomer copolymer type B; cetyl alcohol; citric acid monohydrate; dimethicone 20 Cst; edetate disodium; glycerin; isopropyl palmitate; methyl paraben; oleyl alcohol; phenoxyethanol; polyoxyl 20 cetostearyl ether; propylene glycol; propyl paraben; purified water; sodium hydroxide; sorbitan monostearate and stearyl alcohol.

18. The method of claim 10, wherein the topical administration of the pharmaceutical composition to the subject results in a mean terminal half-life of ivermectin of about 145 hours in the subject.

19. The method of claim 10, wherein the treatment results in about 27% or more median reduction of the inflammatory lesion counts.

* * * * *